United States Patent
Yamamoto et al.

(10) Patent No.: US 6,818,426 B2
(45) Date of Patent: Nov. 16, 2004

(54) (R)-2,3-BUTANEDIOL DEHYDROGENASE

(75) Inventors: Hiroaki Yamamoto, Ibaraki (JP); Keiko Onodera, Nara (JP); Yoshiki Tani, Kyoto (JP)

(73) Assignee: Daicel Chemical Industries, Ltd., Osaka (JP)

(*) Notice: Subject to any disclaimer, the term of this patent is extended or adjusted under 35 U.S.C. 154(b) by 47 days.

(21) Appl. No.: 10/020,674

(22) Filed: Oct. 30, 2001

(65) Prior Publication Data

US 2002/0160468 A1 Oct. 31, 2002

(30) Foreign Application Priority Data

Oct. 31, 2000 (JP) ........................................ 2000-333363

(51) Int. Cl.[7] ............. C12N 9/04; C12N 15/00; C12N 5/00; C12P 7/04; C07H 21/04
(52) U.S. Cl. ...................... 435/190; 435/157; 435/440; 435/325; 536/23.2
(58) Field of Search ................. 435/190, 440, 435/157, 325; 536/23.2

(56) References Cited

U.S. PATENT DOCUMENTS

2003/0032153 A1 * 2/2003 Yamamoto et al. ......... 435/148

FOREIGN PATENT DOCUMENTS

WO      WO 99/54453      10/1999

OTHER PUBLICATIONS

Pharmacia Biotech. Resource Q. pp. 1–4. 1996.*
Gonzalez et al. The Journal of Biological Chemistry. vol. 275, No. 46, pp. 35876–35885, 2000.*
Heidlas et al., "Purification and characterization of a (R)–2,3–butanediol dehydrogenase from *Saccharomyces cerevisiae*", Arch. of Microbiol., 154:267–273, 1990.
Höhn–Bentz et al., "Bacterial 2,3–butanediol Dehydrogenases", Arch. Microbiol., 116:197–203, 1978.
Yamada et al., "Diversity of Glycerol Dehydrogenase in Methylothrophic Yeasts", Agric. Biol. Chem., 51:2401–2407, 1987.
A.M. Smania et al., "Molecular Cloning and Characterization of a cDNA Encoding a Bovine Butanediol Dehydrogenase", *Gene*, 197 (1997) 231–238.
U.S. patent application Ser. No. 10/147,003, Yamamoto et al., filed May 16, 2002.

* cited by examiner

Primary Examiner—Ponnathapu Achutamurthy
Assistant Examiner—Yong D. Pak
(74) Attorney, Agent, or Firm—Fish & Richardson P.C.

(57) ABSTRACT

The objective of the present invention is to produce a novel (R)-2,3-butanediol dehydrogenase useful for the production of ketones, alcohols, and particularly optically active vicinal diols. It has been found that *Pichia angusta* produces novel (R)-2,3-butanediol dehydrogenase that shows the high activity and high stereoselectivity. Further, polynucleotide encoding this (R)-2,3-butanediol dehydrogenase was cloned, and the nucleotide sequence thereof was determined. The expression of the glycerol dehydrogenase was carried out in heterologous microorganisms.

36 Claims, 6 Drawing Sheets

(R)-2,3-BUTANEDIOL DEHYDROGENASE

This application claims priority under 35 USC §119 to Japanese Patent Application No. 2000-333363, filed Oct. 31, 2000, hereby incorporated by reference in its entirety.

TECHNICAL FIELD

The present invention relates to a novel nicotinamide adenine dinucleotide-dependent (R)-2,3-butanediol dehydrogenase. The present invention also relates to a polynucleotide encoding the enzyme protein, a method for producing the enzyme and a method for producing alcohol, particularly (2R,3R)-2,3-butanediol, by using the enzyme.

BACKGROUND (R)-2,3-butanediol dehydrogenase is an enzyme which plays important roles in fermentation production of (2R,3R)-2,3-butanediol with microorganisms using glucose as raw material and in 2,3-butanediol metabolism in microorganisms. Further (2R,3R)-2,3-butanediol generated via the enzyme reaction is a useful compound as raw material for the synthesis of liquid crystal, pharmaceuticals, etc.

(R)-2,3-butanediol dehydrogenase is a dehydrogenase having the activity of selectively oxidizing the hydroxyl group of 2,3-butanediol in (R) configuration and also has the activity of oxidizing the hydroxyl group of meso-2,3-butanediol in (R) configuration as well as that of (2R,3R)-2,3-butanediol in (R) configuration.

Previously, regarding the enzyme having the activity of 2,3-butanediol dehydrogenation, it has been reported dehydrogenase activity toward (2R,3R)-2,3-butanediol is contained, for example, in the microorganisms listed below, based on studies concerning biosynthesis and metabolism of 2,3-butanediol (Arch. Microbiol., 116:197–203, 1978; J. Ferment. Technol., 61:467–471, 1983; J. Ferment. Technol., 62:551–559, 1984). However a variety of natures such as stereoselectivity and specific activity of 2,3-butanediol dehydrogenase was unclear in such previous studies because assays for the activity were conducted by using only cell-free extract and thus various enzymes coexisted:

*Aeromonas hydrophila;*
*Bacillus cereus* IAM 1072;
*Bacillus coagulans* ATCC 8038;
*Micrococcus lysodeikticus* IAM 1056;
*Micrococcus luteus* IAM 1097;
*Micrococcus roseus* IAM 1295;
*Pseudomonas saccharophila* IAM 1504;
*Sarcina lutea* IAM 1099;
*Staphylococcus aureus.*

With respect to enzymes highly purified and having a variety of natures clarified, the following enzymes have been shown to have the activity of 2,3-butanediol dehydrogenase. However, these contain only the activity of catalyzing DL-form and there is no report on the stereoselectivity. Furthermore, the activities of the 2,3-butanediol dehydrogenases with the exception of *Pichia ofunaensis* are comparable to or lower than the activity of glycerol dehydrogenase and thus the specific activities are generally lower.

Glycerol dehydrogenase derived from *Achromobacter liquidum* (*Achromobacter liquidum* KY 3047) (Examined Published Japanese Patent Application No. (JP-B) Sho 58-40467);
Glycerol dehydrogenase derived from *Bacillus* sp. (*Bacillus* sp. G-1) (JP-B Hei 03-72272);
Glycerol dehydrogenase derived from *Bacillus stearothermophilus* (Biochim. Biophys. Acta., 994:270–279, 1989);
Glycerol dehydrogenase derived from *Citrobacter freundii* (*Citrobacter freundii* DSM 30040) (J. Bacteriol., 177:4392–4401, 1995);
Glycerol dehydrogenase derived from *Erwinia aroideae* (*Erwinia aroideae* IFO 3830) (Chem. Pharm. Bull., 26:716–721, 1978);
Glycerol dehydrogenase derived from *Geotrichum candidum* (*Geotrichum candidum* IFO 4597) (JP-B Hei 01-27715);
Dihydroxyacetone reductase derived from *Pichia ofunaensis* (*Pichia ofunaensis* AKU 4328) (J. Biosci. Bioeng., 88:148–152, 1999);
Glycerol dehydrogenase derived from *Schizosaccharomyces pombe* (J. Gen. Microbiol., 131:1581–1588, 1985).

A known enzyme highly purified and having a clarified high selectivity to (2R,3R) isomer of 2,3-butanediol is glycerol dehydrogenase produced by *Escherichia coli* (*Escherichia coli* W-1485) (J. Biol. Chem., 259:2124–2129, 1984). Because Vmax of this enzyme toward (2R,3R)-2,3-butanediol is 28.0 U/mg protein and Vmax toward racemic body is 21.2 U/mg protein, the enzyme is suggested to exhibit the stereoselectivity to (2R,3R) isomer. Here, 1 U of the enzyme is defined as an enzyme activity of reducing 1 $\mu$mol oxidized nicotinamide adenine dinucleotide (hereinafter abbreviated to $NAD^+$) into reduced nicotinamide adenine dinucleotide (hereinafter abbreviated to NADH) for one minute in the presence of (2R,3R)-2,3-butanediol as a substrate.

Further it has been reported that (R)-2,3-butanediol dehydrogenase derived from *Saccharomyces cerevisiae* produces (2R,3R)-2,3-butanediol from 2,3-butanedione (Arch. Microbiol., 154:267–273, 1990), but the dehydrogenase activity to DL-2,3-butanediol is about 20.3 U/mg protein; all of the above exhibit merely low specific activities.

In addition, the gene encoding 2,3-butanediol dehydrogenase participating in the metabolism of 2,3-butanediol has been cloned from *Pseudomonas putida* and expressed in *E. coli* (FEMS Microbiol. Lett., 124(2): 141–150, 1994), but the stereoselectivity has not yet been reported. Further genomic analysis has identified a gene from *Pseudomonas aeruginosa*, which has high homology to the 2,3-butanediol dehydrogenase gene derived from *Pseudomonas putida*. However this gene has not yet been expressed recombinantly and thus neither enzyme activity nor stereoselectivity has been verified.

The followings are industrially important challenges; the discovery of (R)-2,3-butanediol dehydrogenase that is useful for producing optically active alcohols such as (2R,3R)-2,3-butanediol, high stereoselectivity and high specific activity; particularly, the isolation of gene encoding the enzyme and preparation of transformants capable of expressing the enzyme to make it possible to conveniently produce the enzyme on a large scale.

SUMMARY

An objective of the present invention is to provide (R)-2,3-butanediol dehydrogenase that can use $NAD^+$ as a coenzyme. Another objective of the present invention is to provide (R)-2,3-butanediol dehydrogenase capable of giving products of high optical purity in high yield when it is utilized in an enzymatic production process of optically active (2R,3R)-2,3-butanediol using 2,3-butanedione as a substrate.

Yet another objective of the present invention is to isolate a polynucleotide encoding (R)-2,3-butanediol dehydrogenase having desired properties and to obtain a recombinant thereof. In addition, still another objective is to provide a method for enzymatically producing optically active (2R, 3R)-2,3-butanediol by using the novel (R)-2,3-butanediol dehydrogenase.

The present inventors have studied a group of enzymes participating in glycerol metabolism in *Pichia angusta* (previous name: *Hansenula polymorpha*) (Agri. Biol. Chem., 51:2401–2407, 1987). There are two glycerol metabolism pathways, namely phosphorylation pathway and oxidation pathway, in this fungal strain; thus it has been clarified that the strain has both glycerol dehydrogenase I (GDH-I) catalyzing reduction reaction using NADH and dibydroxyacetone as substrates at pH 6.0 as well as glycerol dehydrogenase II (GDH-II) catalyzing oxidation reaction using NAD$^+$ and glycerol as substrates at pH 9.0.

One of these two types of enzymes, GDH-I, was purified to a single band in electrophoresis and a variety of natures thereof have been clarified. The result showed that GDH-I is a novel (R)-2,3-butanediol dehydrogenase having the high activity as well as high selectivity to the hydroxyl group of 2,3-butanediol in (R) configuration.

Further, the present inventor isolated a polynucleotide encoding this enzyme and prepared recombinant bacteria overexpressing this enzyme, thereby completing the present invention. Specifically the present invention relates to the following (R)-2,3-butanediol dehydrogenase, a polynucleotide encoding this enzyme, a method for producing this enzyme and uses thereof.

[1] An (R)-2,3-butanediol dehydrogenase having the following physicochemical properties (1) to (3):

(1) Action
The dehydrogenase produces (R)-acetoin by acting on (2R,3R)-2,3-butanediol using nicotinamide adenine dinucleotide as a coenzyme. The dehydrogenase produces (2R,3R)-2,3-butanediol by reducing 2,3-butanedione using reduced form of nicotinamide adenine dinucleotide as a coenzyme;

(2) Substrate specificity
The dehydrogenase uses nicotinamide adenine dinucleotide as a coenzyme in oxidation reaction. The dehydrogenase uses reduced form of nicotinamide adenine dinucleotide as a coenzyme in reduction reaction. In addition, the dehydrogenase preferentially oxidizes a hydroxyl group of 2,3-butanediol in (R) configuration; and (3) Specific activity:
The dehydrogenase has 100 U or higher of (R)-2,3-butanediol dehydrogenase activity per 1 mg of the dehydrogenase when purified.

[2] The (R)-2,3-butanediol dehydrogenase of [1], wherein the dehydrogenase further has the following physicochemical properties (4) and (5):

(4) Optimal pH
Optimal pH for glycerol oxidation reaction is 10; and (5) Molecular weight
Molecular weight of a subunit of the dehydrogenase is 36,000 when determined by sodium dodecyl sulfate-polyacrylamide gel electrophoresis and molecular weight of the dehydrogenase is 76,000 when determined by gel filtration.

[3] The (R)-2,3-butanediol dehydrogenase of [1], wherein the dehydrogenase is produced by a microorganism belonging to the genus *Pichia*.

[4] The (R)-2,3-butanediol dehydrogenase of [3], wherein the microorganism is *Pichia angusta*.

[5] A polynucleotide of (a) to (d) below:
(a) a polynucleotide comprising the nucleotide sequence of SEQ ID NO:1;
(b) a polynucleotide encoding a polypeptide comprising the amino acid sequence of SEQ ID NO:2;
(c) a polynucleotide encoding a polypeptide that comprises an amino acid sequence comprising the amino acid sequence of SEQ ID NO:2 in which one or more amino acids are substituted, deleted, inserted, and/or added and that is functionally equivalent to a polypeptide comprising the amino acid sequence of SEQ ID NO:2; and
(d) a polynucleotide that hybridizes under stringent conditions to a polynucleotide comprising the nucleotide sequence of SEQ ID NO:1 and that encodes a polypeptide functionally equivalent to a polypeptide comprising the amino acid sequence of SEQ ID NO:2.

[6] The polynucleotide of [5], wherein the polynucleotide comprises a nucleotide sequence having 70% or higher percent identity to the nucleotide sequence of SEQ ID NO:1.

[7] The polynucleotide of [5], wherein the polynucleotide encodes an amino acid sequence having 70% or higher percent identity to the amino acid sequence of SEQ ID NO:2.

[8] A polypeptide encoded by the polynucleotide of [5].

[9] The polypeptide of [8], wherein the polypeptide comprises the amino acid sequence of SEQ ID NO:2.

[10] A vector comprising the polynucleotide of [5].

[11] A transformant comprising the polynucleotide of [5] or the vector of [10].

[12] A method for producing the polypeptide of [9], the method comprising the steps of:
culturing the transformant of [11] and
recovering an expression product.

[13] A method for producing the dehydrogenase of [1] or the polypeptide of [8], the method comprising culturing a microorganism that belongs to the genus *Pichia* and that produces the dehydrogenase of [1] or the polypeptide of [8].

[14] The method of [13], wherein the microorganism is *Pichia angusta*.

[15] A method for producing an alcohol, the method comprising the steps of:
reacting a substance having (R)-2,3-butanediol dehydrogenase activity to a ketone in the presence of reduced form of nicotinamide adenine dinucleotide to generate the alcohol, wherein the substance is selected from the group consisting of the (R)-2,3-butanediol dehydrogenase of [1], the polypeptide of [8], a microorganism producing any one of them, and a processed product thereof, and
recovering the generated alcohol.

[16] The method of [15], wherein the microorganism is the transformant of [11].

[17] The method of [15], wherein the ketone is 2,3-butanedione and the alcohol is (2R,3R)-2,3-butanediol.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
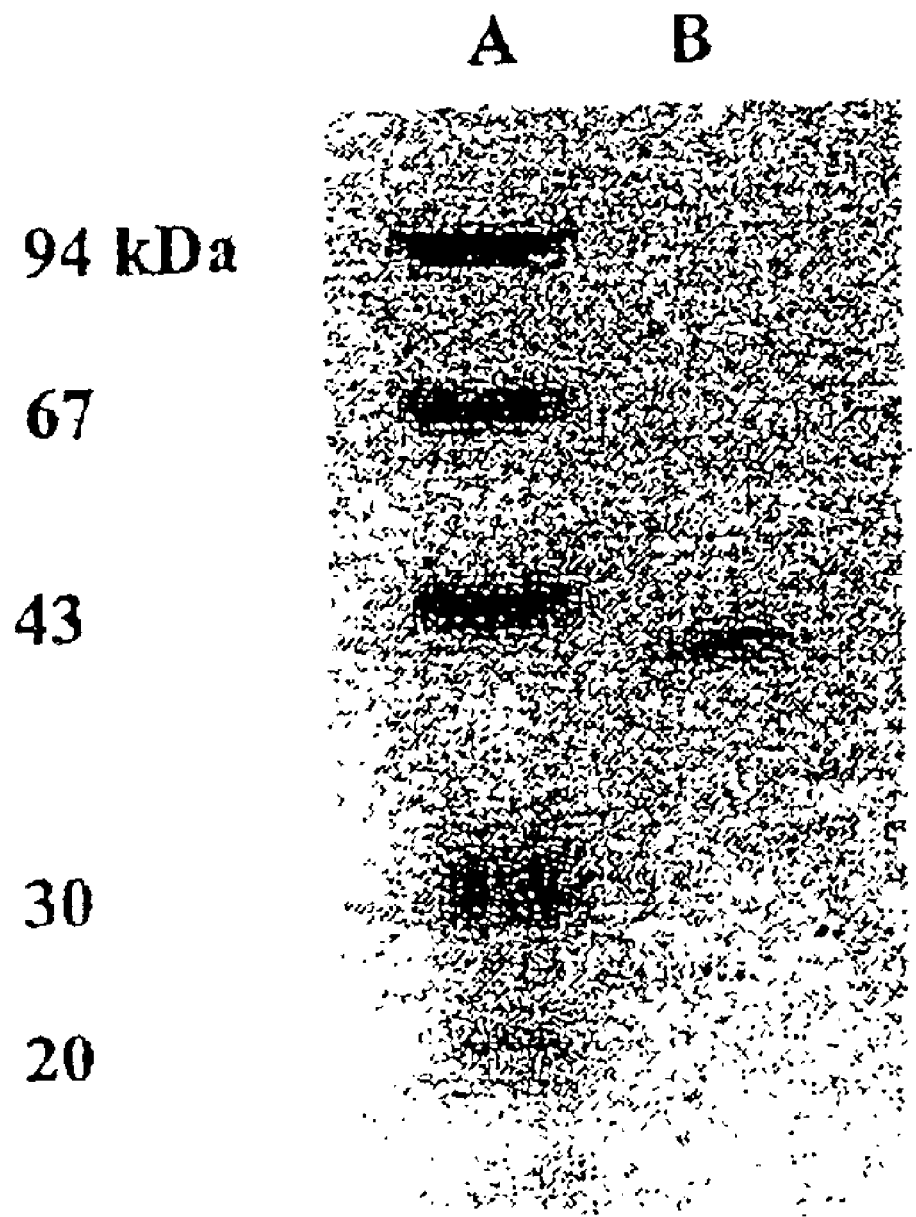
FIG. 1 is a photograph showing an analytical result of concentrated fractions exhibiting glycerol dehydrogenase activity by SDS-PAGE.

The (R)-2,3-butanediol dehydrogenase of the present invention is characterized by the usability of $NAD^+$ as a coenzyme, preferentially oxidizing the hydroxyl group of 2,3-butanediol in (R) configuration, and producing (2R,3R)-2,3-butanediol via reduction of 2,3-butanedione using NADH as a coenzyme.

In the present invention, the enzyme activity of (R)-2,3-butanediol dehydrogenase is represented as the activity of oxidizing glycerol and (2R,3R)-2,3-butanediol, which can be tested as follows.

Assay for the activity of oxidizing (2R,3R)-2,3-butanediol: A reaction mixture, which contains 100 mM potassium phosphate buffer (pH 8.0), 2.5 mM NADH, 50 mM (2R,3R)-2,3-butanediol and the enzyme, is allowed to react at 30° C., and the increase in absorbance at 340 nm, which is associated with the increase in the amount of NADH, is measured. 1 U is defined as the amount of enzyme capable of catalyzing 1 $\mu$mol increase of NADH for one minute. The quantification of polypeptide is carried out by a dye-binding method using a protein assay kit from BioRad.

A reaction mixture containing 100 mM potassium phosphate buffer (pH 8.0), 2.5 mM NADH, 100 mM glycerol and the enzyme is allowed to react at 30° C., and the increase in absorbance at 340 nm, which is associated with the increase in the amount of NADH, is measured. 1 U is defined as the amount of enzyme capable of catalyzing the increase of 1 $\mu$mol NADH for one minute.

Herein, that (R)-2,3-butanediol dehydrogenase "preferentially" oxidizes a hydroxyl group of 2,3-butanediol in (R) configuration means that the enzymatic activity of (R)-2,3-butanediol dehydrogenase on a hydroxyl group of 2,3-butanediol in (S) configuration is 20 or less, preferably 10 or less, and more preferably 5 or less when taking the activity on a hydroxyl group of 2,3-butanediol in (R) configuration as 100.

(R)-2,3-butanediol dehydrogenase having the above physicochemical properties can be purified, for example, from cultures of yeasts belonging to the genus *Pichia*. *Pichia angusta*, among yeasts belonging to the genus *Pichia*, is particularly excellent in the production of (R)-2,3-butanediol dehydrogenase of the present invention. *Pichia angusta*, which can be used to obtain (R)-2,3-butanediol dehydrogenase of the present invention, is available, for example, as ATCC 26012 from American Type Culture Collection.

The above-mentioned microorganism can be cultured in a medium that is generally used for the cultivation of fungi, such as YPD medium (medium containing 1% yeast extract, 1% peptone, and 2% glucose (pH 6.0)). To produce the (R)-2,3-butanediol dehydrogenase of the present invention, it is also possible to use YPD medium in which methanol or glycerol is substituted for glucose; a medium (pH 7.0) containing 1 g of methanol, 0.5 g of ammonium chloride, 0.1 g of potassium dihydrogen phosphate, 0.1 g of dipotassium monohydrogen phosphate, 0.05 g of magnesium sulfate heptahydrate, 3.0 mg of iron (III) chloride hexahydrate, 1.0 mg of calcium chloride dihydrate, 1.0 mg of manganese chloride tetrahydrate, 1.0 mg of zinc sulfate heptahydrate, 200 mg of thiamine hydrochloride and 2 mg of biotin per 100 mL of medium (hereinafter abbreviated to medium A); and medium A in which glycerol is substituted for methanol.

After cultivated by using any one of these culture media, the fungal cells in logarithmic growth phase can be harvested to obtain fungal cells having the high enzyme activity. Further, the fungal cells containing a larger amount of the enzyme can be prepared under conditions where the aeration is a little suppressed in the culture.

The resulting fungal cells are lysed in a buffer containing reducing agents such as 2-mercaptoethanol, and protease inhibitors such as phenylmethansulfonyl fluoride (PMFS), ethylenediamine tetraacetic acid (hereinafter abbreviated to EDTA), pepstatin, leupeptin, and phosphoramidon by using physical impact, e.g., using glass beads, or by high pressure, e.g., using Minilab or French press, to obtain cell-free extract. The enzyme of the present invention can be purified from the cell-free extract by properly combining solubility-dependent protein fractionation (precipitation by organic solvents such as acetone and dimethylsulfoxide or by salting out with ammonium sulfate), cation exchange chromatography, anion exchange chromatography, gel filtration, hydrophobic chromatography, and affinity chromatography using chelate, dye, and antibody. For example, the cell-free extract can be purified to an almost single band in electrophoresis by the combined use of column-chromatographic procedures such as blue-Sepharose, phenyl-Sepharose, and Resource Q (all are provided by Pharmacia).

The *Pichia angusta*-derived (R)-2,3-butanediol dehydrogenase of the present invention is a polypeptide having the following physicochemical properties (1) to (3):

(1) The dehydrogenase produces (R)-acetoin by acting on (2R,3R)-2,3-butanediol using $NAD^+$ as a coenzyme. The dehydrogenase produces (2R,3R)-2,3-butanediol by reducing 2,3-butanedione using NADH as a coenzyme;

(2) The dehydrogenase uses $NAD^+$ as a coenzyme in oxidation reaction and uses NADH as a coenzyme in reduction reaction. In addition, the dehydrogenase preferentially oxidizes a hydroxyl group of 2,3-butanediol in (R) configuration; and (3) The dehydrogenase has 100 U or higher of (R)-2,3-butanediol dehydrogenase activity per 1 mg of the dehydrogenase when purified.

The enzyme of the present invention is a polypeptide further having the following physicochemical properties (4) and (5):

(4) Optimal pH

Optimal pH for glycerol oxidation reaction is 10; and (5) Molecular weight:

Molecular weight of a subunit of the dehydrogenase is 36,000 when determined by sodium dodecyl sulfate-polyacrylamide gel electrophoresis (hereinafter abbreviated to SDS-PAGE) and molecular weight of the dehydrogenase is 76,000 when determined by gel filtration.

Furthermore the enzyme of the present invention is characterized by the following properties (6) to (9):

(6) Stable pH range

The dehydrogenase is relatively stable in the range of pH 6 to 9.5.

(7) Optimal working temperature range

The optimal temperature is 30° C.

(8) Thermal stability:

The dehydrogenase is relatively stable up to 30° C.

(9) Inhibition:

The dehydrogenase is inhibited by p-chloromercuribenzoic acid (PCMB), which is an SH reagent, o-phenanthrolin, 2,2'-bipyridyl, copper chloride, mercury chloride, and iron (III) chloride and not by EDTA.

It is substantially impossible for (R)-2,3-butanediol dehydrogenase derived from *Pichia angusta* to utilize $NADP^+$ as a coenzyme in oxidation reaction and NADPH as a coenzyme in reduction reaction. However, regardless of the usability of $NADP^+$ and NADPH, an enzyme having the above-mentioned physicochemical properties (1) to (3), preferably (1) to (6), and even more preferably (1) to (9) is included in the present invention.

The present invention relates to isolated polynucleotides encoding (R)-2,3-butanediol dehydrogenase and homologues thereof.

As used herein, an "isolated polynucleotide" is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide. Specifically excluded from this definition are polynucleotides of DNA molecules present in mixtures of different (i) DNA molecules, (ii) transfected cells, or (iii) cell clones; e.g., as these occur in a DNA library such as a cDNA or genomic DNA library.

Accordingly, in one aspect, the invention provides an isolated polynucleotide that encodes a polypeptide described herein or a fragment thereof. Preferably, the isolated polynucleotide includes a nucleotide sequence that is at least 60% identical to the nucleotide sequence shown in SEQ ID NO:1. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO:1. In the case of an isolated polynucleotide which is longer than or equivalent in length to the reference sequence, e.g., SEQ ID NO:1, the comparison is made with the full length of the reference sequence. Where the isolated polynucleotide is shorter than the reference sequence, e.g., shorter than SEQ ID NO:1, the comparison is made to segment of the reference sequence of the same length (excluding any loop required by the homology calculation).

Herein, the polynucleotides may be artificial molecules containing artificial nucleotide derivatives in addition to naturally occurring polynucleotides such as DNA and RNA.

Further the polynucleotides of the present invention can be chimeric molecules between DNA and RNA. The polynucleotide encoding the (R)-2,3-butanediol dehydrogenase of the present invention contains, for example, the nucleotide sequence of SEQ ID NO:1. The nucleotide sequence of SEQ ID NO:1 encodes a polypeptide comprising the amino acid sequence of SEQ ID NO:2, and the polypeptide comprising this amino acid sequence provides a preferable embodiment of (R)-2,3-butanediol dehydrogenase in accordance with the present invention.

A homologue of the polynucleotide encoding the (R)-2,3-butanediol dehydrogenase of the present invention includes a polynucleotide having the amino acid sequence of SEQ ID NO:2 in which one or more amino acids are deleted, substituted, inserted and/or added, and which encodes a polypeptide having the above physicochemical properties (1) to (3). Those skilled in the art can readily obtain such a homologue of the polynucleotide by properly introducing substitution, deletion, insertion, and/or addition mutations into the polynucleotide of SEQ ID NO:1 by site-directed mutagenesis (Nucleic Acid Res., 10:6487, 1982; Methods in Enzymol., 100:448, 1983; Molecular Cloning $2^{nd}$ Ed., Cold Spring Harbor Laboratory Press (1989); PCR A Practical Approach IRL Press pp. 200 (1991)) or the like.

Further, the homologue of the polynucleotide of the present invention includes a polynucleotide hybridizing to a polynucleotide comprising the nucleotide sequence of SEQ ID NO:1 under stringent conditions, and which encodes a polypeptide having the above physicochemical properties (1) to (3). A polynucleotide hybridizing under stringent conditions means a polynucleotide hybridizing when polynucleotides selected from one or more sequences containing at least consecutive 20, preferably at least consecutive 30, for example, consecutive 40, 60 or 100 residues that are arbitrarily selected from the sequence of SEQ ID NO:1, are used as probe polynucleotides, for example, by using an ECL direct nucleic acid labeling and detection system (Amersham Pharmaica Biotech) under the conditions as described in the manual (wash: 42° C., primary wash buffer containing 0.5×SSC). Also included in the invention is a polynucleotide that hybridizes under high stringency conditions to the nucleotide sequence of SEQ ID NO:1 or a segment thereof as described herein. "High stringency conditions" refers to hybridization in 6×SSC at about 45° C., followed by one or more washes in 0.2×SSC, 0.1% SDS at 65° C.

Further, the polynucleotide homologue of the present invention includes a polynucleotide encoding a polypeptide having an amino acid sequence exhibiting at least 70%, preferably at least 80% or 90%, more preferably 95% or higher percent identity to the amino acid sequence of SEQ ID NO:2. As used herein, "percent identity" of two amino acid sequences or of two nucleic acids is determined using the algorithm of Karlin and Altschul (Proc. Natl. Acad. Sci. USA, 87:2264–2268, 1990) modified as in Karlin and Altschul (Proc. Natl. Acad. Sci. USA, 90:5873–5877, 1993). Such an algorithm is incorporated into the NBLAST and XBLAST programs of Altschul et al. (J. Mol. Biol., 215:403–410, 1990). BLAST nucleotide searches are performed with the NBLAST program, score=100, wordlength=12. Homology search of protein can readily be performed, for example, in DNA Databank of JAPAN (DDBJ), by using the FASTA program, BLAST program, etc. BLAST protein searches are performed with the XBLAST program, score=50, wordlength=3. Where gaps exist between two sequences, Gapped BLAST is utilized as described in Altsuchl et al. (Nucleic Acids Res., 25:3389–3402, 1997). When utilizing BLAST and Gapped BLAST programs, the default parameters of the respective programs (e.g, XBLAST and NBLAST) are used. Homology search of protein can be achieved, for example, on the Internet by using a program such as BLAST, FASTA, and such, for example, in databases related to amino acid sequence of proteins, such as SWISS-PROT, PIR, and such; databases related to DNA sequences, such as DDBJ, EMBL, GenBank, and such; databases related to deduced amino acid sequences based on DNA sequences; and such.

As a result of homology search in SWISS-PROT for the amino acid sequence of SEQ ID NO:2 by using BLAST program, YAGO derived from *Saccharomyces cerevisiae* exhibited the highest percent identity among known proteins. YAGO is a hypothetical alcohol dehydrogenase-like protein (HYPOTHETICAL ZINC-TYPE ALCOHOL DEHYDROGENASE-LIKE PROTEIN) predicted from the result of genome analysis, but the presence as a protein, function, physicochemical properties thereof, and such remain to be clarified. The homology to YAGO was 46% in "Identity" and 62% in "Positive". Herein, 70% or higher percent identity indicates, for example, the value of homology in Positive using BLAST program.

The present invention relates to a substantially pure polypeptide comprising the amino acid sequence of SEQ ID NO:2. Further the present invention includes a homologue of the polypeptide comprising the amino acid sequence of SEQ ID NO:2.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel elecrophoresis, or HPLC analysis.

A homologue of the (R)-2,3-butanediol dehydrogenase of the present invention means a polypeptide comprising of the amino acid sequence of SEQ ID NO:2 in which one or more amino acids are deleted, substituted, inserted and/or added, and which is functionally equivalent to a polypeptide comprising the amino acid sequence of SEQ ID NO:2. In the present invention, "functionally equivalent to a polypeptide comprising the amino acid sequence of SEQ ID NO: 2" means that the polypeptide has the above-mentioned physicochemical properties (1) to (3). Those skilled in the art can obtain a polynucleotide encoding a homologue of (R)-2,3-butanediol dehydrogenase by properly introducing substitution, deletion, insertion, and/or addition mutations into the polynucleotide of SEQ ID NO:1 by site-directed mutagenesis (Nucleic Acid Res., 10:6487, 1982; Methods in Enzymol., 100:448, 1983; Molecular Cloning $2^{nd}$ Ed., Cold Spring Harbor Laboratory Press (1989); PCR A Practical Approach IRL Press pp.200 (1991)) or the like. It is possible to obtain a homologue of (R)-2,3-butanediol dehydrogenase of SEQ ID NO:2 by introducing and expressing a polynucleotide encoding the homologue of (R)-2,3-butanediol dehydrogenase in a host.

The number of amino acids that are mutated is not particularly restricted, as long as the (R)-2,3-butanediol dehydrogenase activity is maintained. Normally, it is within 50 amino acids, preferably within 30 amino acids, more preferably within 10 amino acids, and even more preferably within 3 amino acids. The site of mutation may be any site, as long as the (R)-2,3-butanediol dehydrogenase activity is maintained.

An amino acid substitution is preferably mutated into different amino acid(s) in which the properties of the amino acid side-chain are conserved. A "conservative amino acid substitution" is a replacement of one amino acid residue belonging to one of the following groups having a chemically similar side chain with another amino acid in the same group. Groups of amino acid residues having similar side chains have been defined in the art. These groups include amino acids with basic side chains (e.g., lysine, arginine, histidine), acidic side chains (e.g., aspartic acid, glutamic acid), uncharged polar side chains (e.g., glycine, aspargine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Further, the homologue of the (R)-2,3-butanediol dehydrogenase of the present invention is a polypeptide having an amino acid sequence exhibiting at least 70%, preferably at least 80% or 90%, more preferably 95% or higher percent identity to the amino acid sequence of SEQ ID NO:2. Homology search of protein can be achieved, for example, on the Internet by using a program such as BLAST, FASTA, and such, for example, in databases related to amino acid sequence of proteins, such as SWISS-PROT, PIR, and such; databases related to DNA sequences, such as DDBJ, EMBL, GenBank, and such; databases related to deduced amino acid sequences based on DNA sequences; and such.

The polynucleotide encoding the (R)-2,3-butanediol dehydrogenase of the present invention can be isolated, for example, by the following method.

PCR primers are designed based on the nucleotide sequence of SEQ ID NO:1, and the polynucleotide of the present invention can be obtained by conducting PCR, using the genomic DNA or cDNA library of the enzyme-producing strain as the template.

Moreover, polynucleotide of the present invention can be obtained, with the obtained polynucleotide fragment as the probe, by inserting the restriction enzyme digestion product of the genomic DNA of the enzyme-producing strain into a phage or plasmid and such, by transforming the *E. coli* with it to obtain the library or cDNA library, and by conducting colony hybridization, plaque hybridization, and so on.

It is also possible to obtain the polynucleotide encoding the polypeptide of the present invention by analyzing the nucleotide sequence of the obtained polynucleotide fragment by PCR and by designing a PCR primer to elongate the known polynucleotide outside. After digesting the genomic DNA of the enzyme-producing strain with an appropriate restriction enzyme, reverse PCR is performed using the polynucleotide as the template, by the self cyclization reaction (Genetics, 120:621–623, 1988), the RACE method (Rapid Amplification of cDNA End, "PCR experimental manual" p25–33 HBJ press) and such.

The polynucleotide of the present invention includes not only genomic DNA or cDNA cloned by the above-mentioned methods but also synthesized polynucleotide.

The isolated polynucleotide encoding the (R)-2,3-butanediol dehydrogenase of the present invention is inserted into a known expression vector to provide a (R)-2,3-butanediol dehydrogenase-expressing vector. Further, by culturing cells transformed with the expression vector, the (R)-2,3-butanediol dehydrogenase of the present invention can be obtained from the transformed cells.

Herein, there is no restriction on the microorganism to be transformed for expressing (R)-2,3-butanediol dehydrogenase whose electron acceptor is $NAD^+$, as long as the microorganism is capable of being transformed with a recombinant vector containing a polynucleotide encoding a polypeptide with the activity of (R)-2,3-butanediol dehydrogenase whose electron acceptor is NAD$^+$ and as long as the microorganism is capable of expressing the activity of (R)-2,3-butanediol dehydrogenase whose electron acceptor is NAD$^+$. Available microorganisms are those for which host-vector systems are available and include, for example:

bacteria such as the genus *Escherichia*, the genus *Bacillus*, the genus *Pseudomonas*, the genus *Serratia*, the genus *Brevibacterium*, the genus *Corynebacterium*, the genus *Streptococcus*, and the genus *Lactobacillus*;

actinomycetes such as the genus *Rhodococcus* and the genus *Streptomyces*;

yeasts such as the genus *Saccharomyces*, the genus *Kluyveromyces*, the genus *Schizosaccharomyces*, the genus *Zygosaccharomyces*, the genus *Yarrowia*, the genus *Trichosporon*, the genus *Rhodosporidium*, the genus *Pichia*, and the genus *Candida*; and fungi such as the genus *Neurospora*, the genus *Aspergillus*, the genus *Cephalosporium*, and the genus *Trichoderma*; etc.

Procedure for preparation of a transformant and construction of a recombinant vector suitable for a host can be carried out by employing techniques that are commonly used in the fields of molecular biology, bioengineering, and genetic engineering (for example, see Sambrook et al., "Molecular Cloning", Cold Spring Harbor Laboratories). In order to express, in a microorganism, the gene encoding (R)-2,3-butanediol dehydrogenase of the present invention whose electron donor is NAD$^+$, it is necessary to introduce the polynucleotide into a plasmid vector or phage vector that is stable in the microorganism and to let the genetic information transcribed and translated.

To do so, a promoter, a unit for regulating transcription and translation, is placed upstream of the 5' end of the polynucleotide of the present invention, and preferably a terminator is placed downstream of the 3' end of the polynucleotide. The promoter and the terminator should be functional in the microorganism to be utilized as a host. Available vectors, promoters, and terminators for the above-mentioned various microorganisms are described in detail in "Fundamental Course in Microbiology (8): Genetic Engineering", Kyoritsu Shuppan, specifically for yeasts, in "Adv. Biochem. Eng. 43, 75–102(1990)" and "Yeast 8, 423–488 (1992)."

For example, for the genus *Escherichia*, in particular, for *Escherichia coli*, available plasmids include pBR series and pUC series plasmids; available promoters include promoters derived from lac (derived from β-galactosidase gene), trp (derived from the tryptophan operon), tac and trc (which are chimeras of lac and trp), $P_L$ and $P_R$ of λ phage, etc. Available terminators are derived from trpA, phages, rrnB ribosomal RNA, etc. Among these, a vector pSE420D (described in Unexamined Published Japanese Patent Application No. (JP-A) 2000-189170), which is constructed by partially modifying the multicloning site of commercially available pSE420 (Invitrogen), can be preferably used.

For the genus *Bacillus*, available vectors are pUB110 series and pC194 series plasmids; the vectors can be integrated into host chromosome. Available promoters and terminators are derived from apr (alkaline protease), npr (neutral protease), amy (a-amylase), etc.

For the genus *Pseudomonas*, there are host-vector systems developed for *Pseudomonas putida* and *Pseudomonas cepacia*. A broad-host-range vector, pKT240, (containing RSF1010-derived genes required for autonomous replication) based on TOL plasmid, which is involved in decomposition of toluene compounds, is available; a promoter and a terminator derived from the lipase gene (JP-A Hei 5-284973) are available.

For the genus *Brevibacterium*, in particular, for *Brevibacterium lactofermentum*, available plasmid vectors include pAJ43 (Gene, 39:281, 1985). Promoters and terminators used for *Escherichia coli* can be utilized without any modification for *Brevibacterium*.

For the genus *Corynebacterium*, in particular, for *Corynebacterium glutamicum*, plasmid vectors such as pCS11 (JP-A Sho 57-183799) and pCB101 (Mol. Gen. Genet., 196:175, 1984) are available.

For the genus *Streptococcus*, plasmid vectors such as pHV1301 (FEMS Microbiol. Lett., 26:239, 1985) and pGK1 (Appl. Environ. Microbiol., 50:94, 1985) can be used.

For the genus *Lactobacillus*, plasmid vectors such as pAMb1 (J. Bacteriol., 137:614, 1979), which was developed for the genus *Streptococcus*, can be utilized; and promoters that are used for *Escherichia coli* are also usable.

For the genus *Rhodococcus*, plasmid vectors isolated from *Rhodococcus rhodochrous* are available (J. Gen. Microbiol., 138:1003, 1992).

For the genus *Streptomyces*, plasmids can be constructed in accordance with the method as described in "Genetic Manipulation of Streptomyces: A Laboratory Manual" (Cold Spring Harbor Laboratories (1985)) by Hopwood et al. In particular, for *Streptomyces lividans*, pIJ486 (Mol. Gen. Genet., 203:468–478, 1986), pKC1064 (Gene, 103:97–99, 1991), and pUWL-KS (Gene, 165:149–150, 1995) are usable. The same plasmids can also be utilized for *Streptomyces virginiae* (Actinomycetol., 11:46–53, 1997).

For the genus *Saccharomyces*, in particular, for *Saccharomyces cerevisiae*, YRp series, YEp series, YCp series, and YIp series plasmids are available; integration vectors (refer EP 537456, etc.), which are integrated into chromosome via homologous recombination with multicopy-ribosomal genes, allow to introduce a gene of interest in multicopy and the gene incorporated is stably maintained in the microorganism; and thus, these types of vectors are highly useful. Available promoters and terminators are derived from genes encoding ADH (alcohol dehydrogenase), GAPDH (glyceraldehyde-3-phosphate dehydrogenase), PHO (acid phosphatase), GAL (β-galactosidase), PGK (phosphoglycerate kinase), ENO (enolase), etc.

For the genus *Kluyveromyces*, in particular, for *Kluyveromyces lactis*, available plasmids are those such as 2-mm plasmids derived from *Saccharomyces cerevisiae*, pKD1 series plasmids (J. Bacteriol., 145:382–390, 1981), plasmids derived from pGK11 and involved in the killer activity, KARS (*Kluyveromyces* autonomous replication sequence) plasmids, and plasmids (refer EP 537456, etc.) capable of being integrated into chromosome via homologous recombination with the ribosomal DNA. Promoters and terminators derived from ADH, PGK, and the like are available.

For the genus *Schizosaccharomyces*, it is possible to use plasmid vectors comprising ARS (autonomous replication sequence) derived from *Schizosaccharomyces pombe* and auxotrophy-complementing selectable markers derived from *Saccharomyces cerevisiae* (Mol. Cell. Biol., 6:80, 1986). Promoters such as ADH promoter derived from *Schizosaccharomyces pombe* are usable (EMBO J., 6:729, 1987). In particular, pAUR224 is commercially available from TaKaRa Shuzo Co., Ltd.

For the genus *Zygosaccharomyces*, plasmids originating from those such as pSB3 (Nucleic Acids Res., 13:4267, 1985) derived from *Zygosaccharomyces rouxii* are available;

it is possible to use promoters such as PHO5 promoter derived from *Saccharomyces cerevisiae* and GAP-Zr (Glyceraldehyde-3-phosphate dehydrogenase) promoter (Agri. Biol. Chem., 54:2521, 1990) derived from *Zygosaccharomyces rouxii*.

A Host-vector system has been developed for *Pichia angusta* (previously called *Hansenula polymorpha*) among the genus *Pichia*. Usable vectors include *Pichia angusta*-derived genes (HARS1 and HARS2) involved in autonomous replication, but they are relatively unstable. Therefore, multi-copy integration of the gene into a chromosome is effective (Yeast, 7:431–443, 1991). Promoters of AOX (alcohol oxidase) and FDH (formic acid dehydrogenase), which are induced by methanol and such, are also available. Another host vector system where *Pichia*-derived genes involved in autonomous replication (PARS1 and PARS2) are used in *Pichia pastoris* and such has been developed (Mol. Cell. Biol., 5:3376, 1985), and thus high-density cultivation and strong promoters such as methanol-inducible AOX are usable (Nucleic Acids Res., 15:3859,1987).

For the genus *Candida*, host-vector systems have been developed for *Candida maltosa, Candida albicans, Candida tropicalis, Candida utilis*, etc. An autonomous replication sequence originating from *Candida maltosa* has been cloned (Agri. Biol. Chem., 51, 51:1587, 1987), and a vector using the sequence has been developed for *Candida maltosa*. Further, a chromosome-integration vector with a highly efficient promoter unit has been developed for *Candida utilis* (JP-A Hei. 08-173170).

For the genus *Aspergillus, Aspergillus niger* and *Aspergillus oryzae* have intensively been studied among fungi, and thus plasmid vectors and chromosome-integration vectors are available, as well as promoters derived from an extracellular protease gene and amylase gene (Trends in Biotechnology, 7:283–287, 1989).

For the genus *Trichoderma*, host-vector systems have been developed for *Trichoderma reesei*, and promoters such as that derived from an extracellular cellulase gene are available (Biotechnology, 7:596–603, 1989).

There are various host-vector systems developed for plants and animals other than microorganisms; in particular, the systems include those of insect such as silkworm (Nature, 315:592–594, 1985), and plants such as rapeseed, maize, potato, etc. These systems are preferably employed to express a large amount of foreign polypeptide.

Microorganisms capable of producing (R)-2,3-butanediol dehydrogenase to be utilized in the present invention include all strains, mutants, variants, and transformants that are capable of producing $NAD^+$-dependent (R)-2,3-butanediol dehydrogenase and that belong to the genus *Pichia*, the transformants being created by genetic manipulation and obtaining the capability of producing the enzyme of the present invention.

The present invention relates to the use for producing alcohol, particularly (R)-2,3-butanediol, via reduction of ketone with the above-mentioned (R)-2,3-butanediol dehydrogenase. It is possible to carry out the enzyme reaction of interest by contacting the enzyme molecule, processed product thereof, culture containing the enzyme molecules or live transformants such as microorganisms producing the enzyme, with a reaction solution. The transformant can be used in the form of the culture, cells separated from the culture medium by filtration, centrifugation or the like, or cells resuspended in buffer, water, or the like after they are separated by centrifugation and washed. The separated cells can be used in a state as they are recovered, as their disrupts, as treated with acetone or toluene, or as lyophilizate. When the enzyme is extracellularly produced, the culture medium of the transformant can also be used after it is separated from the transformant by the usual methods. The forms of contacting the enzyme and reaction solution are not limited to these specific examples.

The reaction solution comprises substrate and NADH that is a coenzyme required for the enzyme reaction, both of which are dissolved in a suitable solvent which gives an environment desirable for the enzyme activity. The processed product of microorganism containing (R)-2,3-butanediol dehydrogenase in accordance with the present invention specifically includes microorganism in which permeability of the cell membrane has been altered by a detergent or an organic solvent such as toluene; a cell-free extract obtained by lysing cells of the microorganism with glass beads or by enzyme treatment; and partially purified material thereof.

2,3-butanedione and 2,3-pentadione, which have diketone adjacent to each other, can be used suitably as ketones in the method for producing alcohols according to the present invention.

The present invention relates to the uses for producing ketones via alcohol oxidation reaction by the above-mentioned (R)-2,3-butanediol dehydrogenase. It is possible to carry out the enzyme reaction of interest by contacting the enzyme molecule, processed product thereof, culture containing the enzyme molecules or live transformants such as microorganisms producing the enzyme with a reaction solution. The transformant can be used in the form of the culture, cells separated from the culture medium by filtration, centrifugation or the like, or cells resuspended in buffer, water, or the like after they are separated by centrifugation and washed. The separated cells can be used in a state as they are recovered, as their disrupts, as treated with acetone or toluene, or as lyophilizate. When the enzyme is extracellularly produced, the culture medium of the transformant can also be used after it is separated from the transformant by the usual methods. The form of contacting the enzyme and reaction solution is not limited to these specific examples.

The reaction solution comprises substrate and $NAD^+$ that is a coenzyme required for the enzyme reaction, both of which are dissolved in a suitable solvent which gives an environment desirable for the enzyme activity. The processed product of microorganism containing (R)-2,3-butanediol dehydrogenase in accordance with the present invention specifically includes microorganism in which permeability of the cell membrane has been altered by a detergent or an organic solvent such as toluene; a cell-free extract obtained by lysing cells of the microorganism with glass beads or by enzyme treatment; and partially purified material thereof.

Alcohols to be used in the method for producing ketones in accordance with the present invention include (2R,3R)-2,3-butanediol and meso-2,3-butanediol; (R)-acetoin and (S)-acetoin can be synthesized from the respective compounds.

The regeneration of NADH from $NAD^+$ that is generated from NADH, which is associated with the above reduction reaction, can be achieved by using the ability of microorganism to reduce $NAD^+$ (glycolytic pathway, assimilation pathway for C1 compound of methylotroph, etc.). It is possible to enhance the ability of reducing $NAD^+$ by adding glucose, ethanol, formic acid or the like into the reaction system. Furthermore, it can also be achieved by adding microorganisms capable of generating NADH from $NAD^+$, processed product thereof or the enzyme into the reaction system. For example, the regeneration of NADH can be achieved by using microorganisms containing glucose dehydrogenase, formic acid dehydrogenase, alcohol dehydrogenase, amino acid dehydrogenase, organic acid dehydrogenase (e.g., malate dehydrogenase), etc., processed product thereof or and partially or fully purified enzymes. These components for the reaction required for the regeneration of NADH can be added to reaction system to produce alcohols in accordance with the present invention, can be added after immobilized, or alternatively can be contacted via a membrane where NADH is permeable.

Further, in some cases, additional reaction systems for the regeneration of NADH are unnecessary, when live fungal cells of microorganism transformed with recombinant vector containing the polynucleotide of the present invention is intended to be utilized in the above-mentioned method for producing alcohols. Specifically, when microorganisms having higher activity of regenerating NADH are used, an efficient reaction can be achieved in the reduction reaction using transformants without the addition of the enzyme for the regeneration of NADH. Further, it is possible to more efficiently achieve the expression of enzyme for regenerating NADH and $NAD^+$-dependent (R)-2,3-butanediol dehydrogenase, and thus possible to achieve efficient reduction reaction, by co-introducing a gene for glucose dehydrogenase, formic acid dehydrogenase, alcohol dehydrogenase, amino acid dehydrogenase, and organic acid dehydrogenase (e.g., malate dehydrogenase), which are usable to regenerate NADH, together with a polynucleotide encoding the NADH-dependent (R)-2,3-butanediol dehydrogenase of the present invention into a host. When two or more genes of these are introduced into a host, several methods can be utilized to avoid incompatibility, which include a method where a host is transformed with recombinant vectors constructed by separately inserting the genes into multiple vectors containing different replication origins; a method where both genes are inserted into a single vector; or a method where either or both genes are introduced into a chromosome.

When multiple genes are intended to be inserted into a single vector, it is possible to use a method where regions associated with the expression, such as promoter and terminator, are ligated with each gene and it is possible to express them in a form of operon containing multiple cistrons, such as lactose operon.

It is possible to achieve the reduction reaction using the enzyme of the present invention in water or an organic solvent that is not miscible with water, for example, organic solvents such as ethyl acetate, butyl acetate, toluene, chloroform, and n-hexane, or a heterogeneous two-solvent system containing water solvent. The reaction in accordance with the present invention can be achieved by using immobilized enzyme, membrane reactor or the like.

The reaction in accordance with the present invention can be conducted at a reaction temperature of 4 to 60° C., preferably 15 to 30° C., at pH 3 to 11, preferably pH 6 to 9.5, at a substrate concentration of 0.01 to 90%, preferably 0.1 to 30%. If desired, it is possible to add coenzyme $NAD^+$ or NADH of 0.001 mM-100 mM, preferably of 0.01 to 100 mM, in the reaction system. Further, the substrate can be added at a time at the start of reaction, but it is preferable to add it continuously or stepwise so that the concentration of substrate does not become too high in the reaction mixture.

In the regeneration of NADH, for example, glucose is added to the reaction system when glucose dehydrogenase is intended to be used; formic acid is added when formic acid dehydrogenase is used; ethanol or isopropanol is added when alcohol dehydrogenase is used. These compounds can be added in 0.1 to 20 fold excess, preferably 1 to 5 fold excess over the substrate ketone at a molar ratio. On the other hand, it is possible to add the enzymes for regenerating NADH, such as glucose dehydrogenase, formic acid dehydrogenase and alcohol dehydrogenase, in about 0.1 to 100 fold excess, preferably 0.5 to 20 fold excess in enzyme activity as compared with the NADH-dependent carbonyl dehydrogenase of the present invention.

The purification of alcohol generated by reduction of ketone according to the present invention can be performed by properly combining centrifugal separation of fungal cells and polypeptides, separation with membrane treatment or the like, extraction by solvent, distillation, etc.

For example, with respect to (2R,3R)-2,3-butanediol, highly purified (R)-2,3-butanediol dehydrogenase can be prepared by separating a reaction mixture containing cells of microorganism with centrifugation to remove the cells of microorganism, removing polypeptides by ultrafiltration, adding a solvent such as ethyl acetate to the filtrate for the extraction of (2R,3R)-2,3-butanediol into the solvent layer, and then by distillation following the phase separation.

Provided are $NAD^+$-dependent (R)-2,3-butanediol dehydrogenase useful for the production of optically active alcohol or the like and polynucleotide encoding the enzyme. A method for the efficient production of (2R,3R)-2,3-butanediol with high optical purity was provided by utilizing this enzyme. Because the (R)-2,3-butanediol dehydrogenase of the present invention is dependent on $NAD^+$, which is more stable than $NADP^+$, it can be used conveniently in industrial production processes.

The method for producing (2R,3R)-2,3-butanediol of high optical purity according to the present invention is useful as a method for producing raw materials for liquid crystal, pharmaceuticals, etc.

Any patents, patent applications, and publications cited herein are incorporated by reference.

The present invention is illustrated in detail below with reference to Examples, but is not to be construed as being limited thereto.

Herein, "%" for concentration denotes weight per volume percent unless otherwise specified.

EXAMPLE 1

Purification of (R)-2,3-butanediol dehydrogenase

*Pichia angusta* ATCC 26012 strain was cultured in medium A using 7 L of glycerol as a carbon source at 28° C. for 40 hours and then the wet fungal cells were prepared by centrifugal separation. About 100 g of the resulting wet cells were suspended in 130 mL of 50 mM potassium phosphate buffer (pH 8.0)/1 mM 2-mercaptoethanol, and crushed with a bead-beater (Biospec). Then debris of the fungal cells was removed by centrifugal separation to give a cell-free extract. The cell-free extract was loaded onto Blue Sepharose 6B (2.2 cm×20 cm) equilibrated with buffer A (50 mM potassium phosphate buffer (pH 8.0) and 1 mM 2-mercaptoethanol), and the column was washed with buffer A. Then elution was carried out with a concentration gradient of 0 to 1 M sodium chloride. The eluted fractions exhibiting glycerol dehydrogenase activity were collected.

After dialyzed against buffer A, the concentrated enzyme solution was loaded onto phenyl-Sepharose (1.0 cm×10 cm) equilibrated with 40% ammonium sulfate-saturated buffer A. After the column was washed with the same buffer, the elution was carried out with a gradient of 40 to 0% ammonium sulfate-saturated solution. The eluted fractions exhibiting glycerol dehydrogenase activity were collected, and then they were concentrated by ultrafiltration.

The concentrated enzyme solution was loaded onto a column of resource Q (Resource Q HR 5/5) equilibrated with a buffer containing 20 mM potassium phosphate buffer (pH 8.0) and 1 mM 2-mercaptoethanol and then the column was washed with the same buffer. The elution was carried out with a concentration gradient of 0 to 1 M sodium chloride. The fractions exhibiting the activity were concentrated and analyzed by SDS-PAGE. The result showed that the protein appeared as an almost single band (FIG. 1).

The specific activity of purified enzyme was about 218 U/mg (glycerol dehydrogenase activity; which corresponds to an activity of 1350 U/mg of (2R,3R)-2,3-butanediol dehydrogenase). The purification processes are summarized in Table 1.

TABLE 1

| Step | Protein (mg) | Total activity (U) | Specific activity (U/mg) | Purification Fold |
| --- | --- | --- | --- | --- |
| Cell-free extract | 2400 | 266 | 0.111 | 1 |
| Blue Sepharose | 884 | 195 | 0.221 | 2 |
| Phenyl-Sepharose | 4.0 | 190 | 47.7 | 431 |
| Resource Q | 0.30 | 66.2 | 218 | 1972 |

EXAMPLE 2

Determination of molecular weight of (R)-2,3-butanediol dehydrogenase

The molecular weight of the subunit of the enzyme obtained in Example 1 was determined to be 36,000 by SDS-PAGE. Further the molecular weight was determined to be approximately 76,000 when measured by using a gel filtration column with Superdex G200.

EXAMPLE 3

Optimal pH for (R)-2,3-butanediol dehydrogenase

Figure 2:
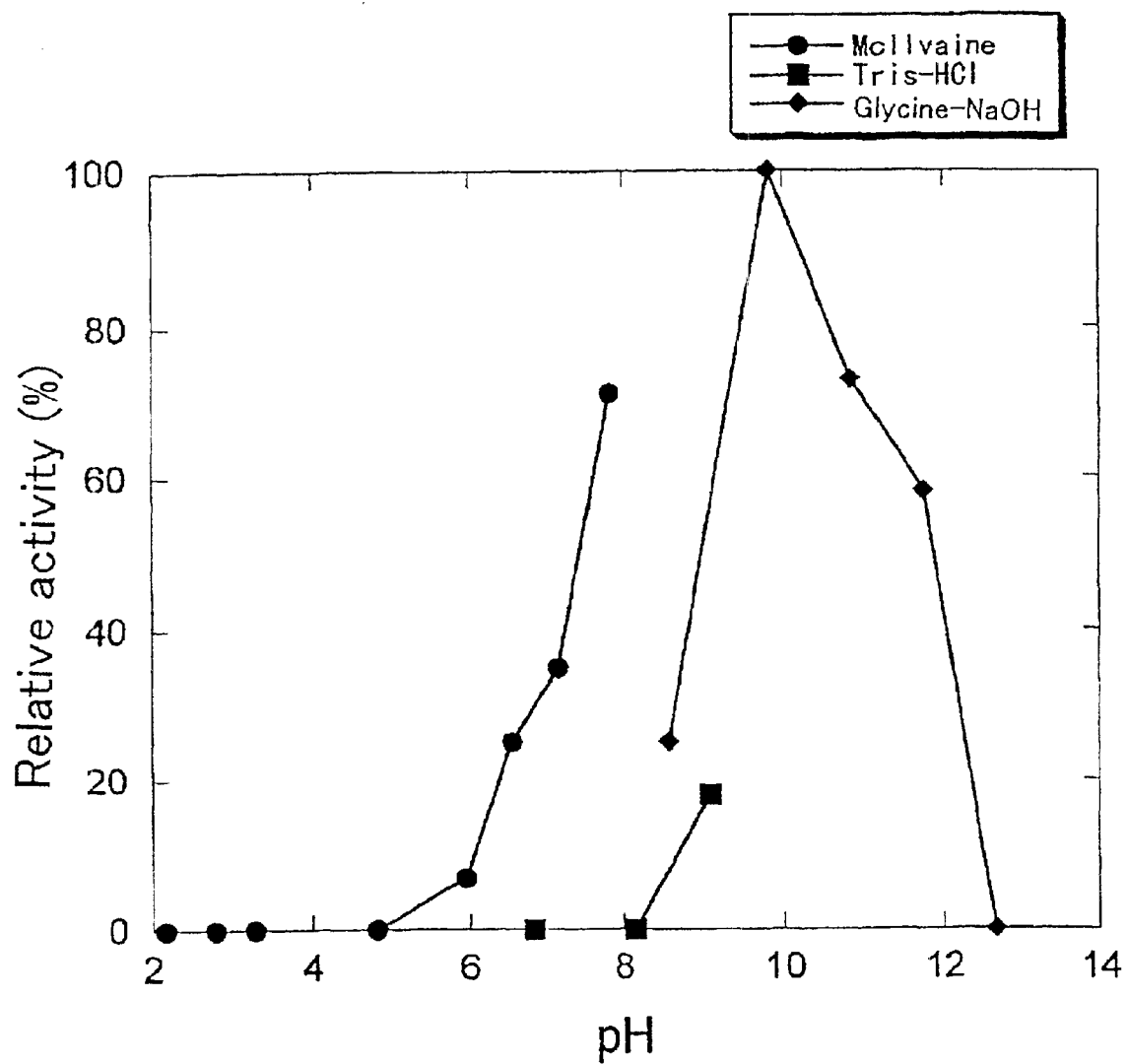
FIG. 2 is a diagram showing a result of measurement to determine the optimal pH for (R)-2,3-butanediol dehydrogenase. The activity is represented by a relative activity when the maximal activity is taken as 100.

Glycerol dehydrogenase activity of the enzyme obtained in Example 1 was tested, while the pH was being altered by using McIlvaine buffer, Tris-HCl buffer, and glycine-NaOH buffer. The activity is represented by a relative activity, taking the maximal activity as 100, and is shown in FIG. 2. The optimal pH for the reaction was 10.

EXAMPLE 4

Optimal temperature for the action of (R)-2,3-butanediol dehydrogenase

Figure 3:
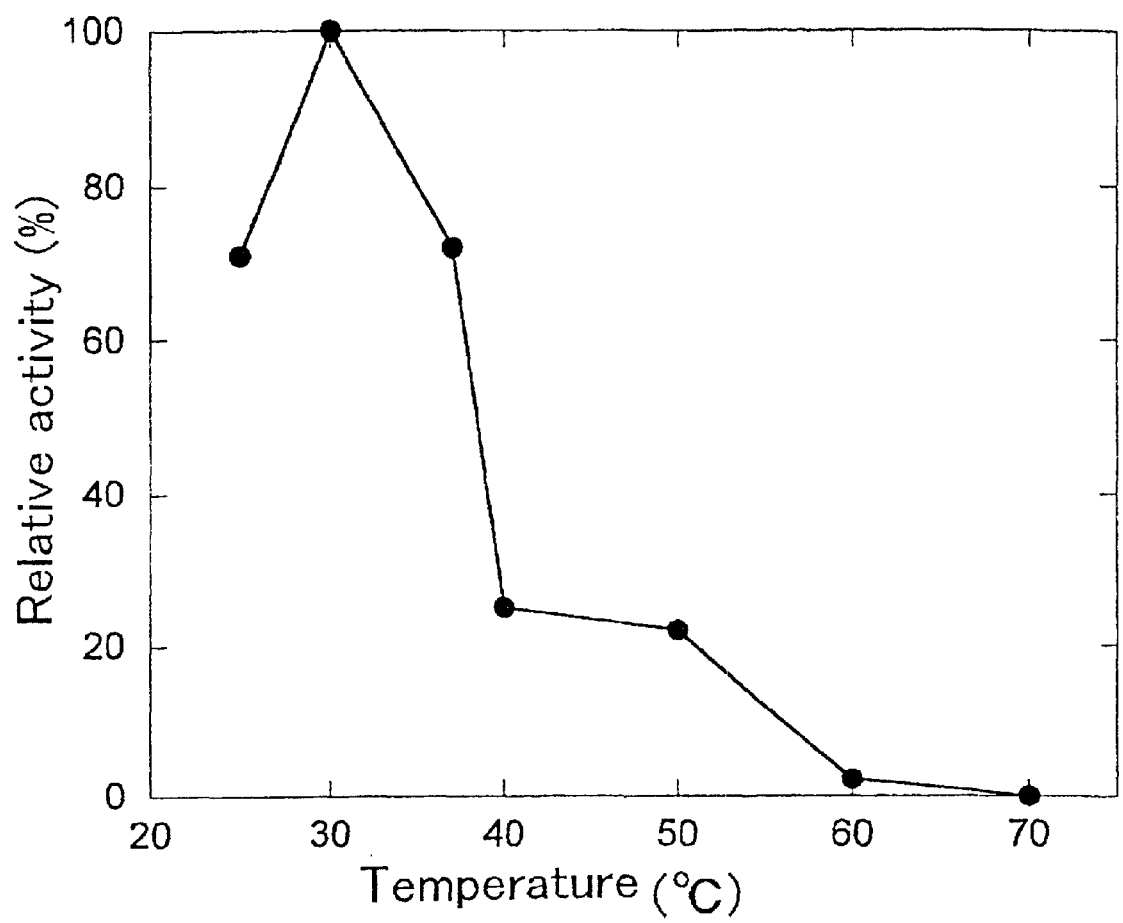
FIG. 3 is a diagram showing a result of measurement to determine the optimal temperature for the action of (R)-2,3-butanediol dehydrogenase. The activity is represented by a relative activity when the maximal activity is taken as 100.

Glycerol dehydrogenase activity of the enzyme obtained in Example 1 was assayed under standard reaction conditions except that only the temperature was altered. The activity is represented by a relative activity, taking the maximal activity as 100, and is shown in FIG. 3. The optimal temperature was 30° C.

EXAMPLE 5 pH stability of (R)-2,3-butanediol dehydrogenase

Figure 4:
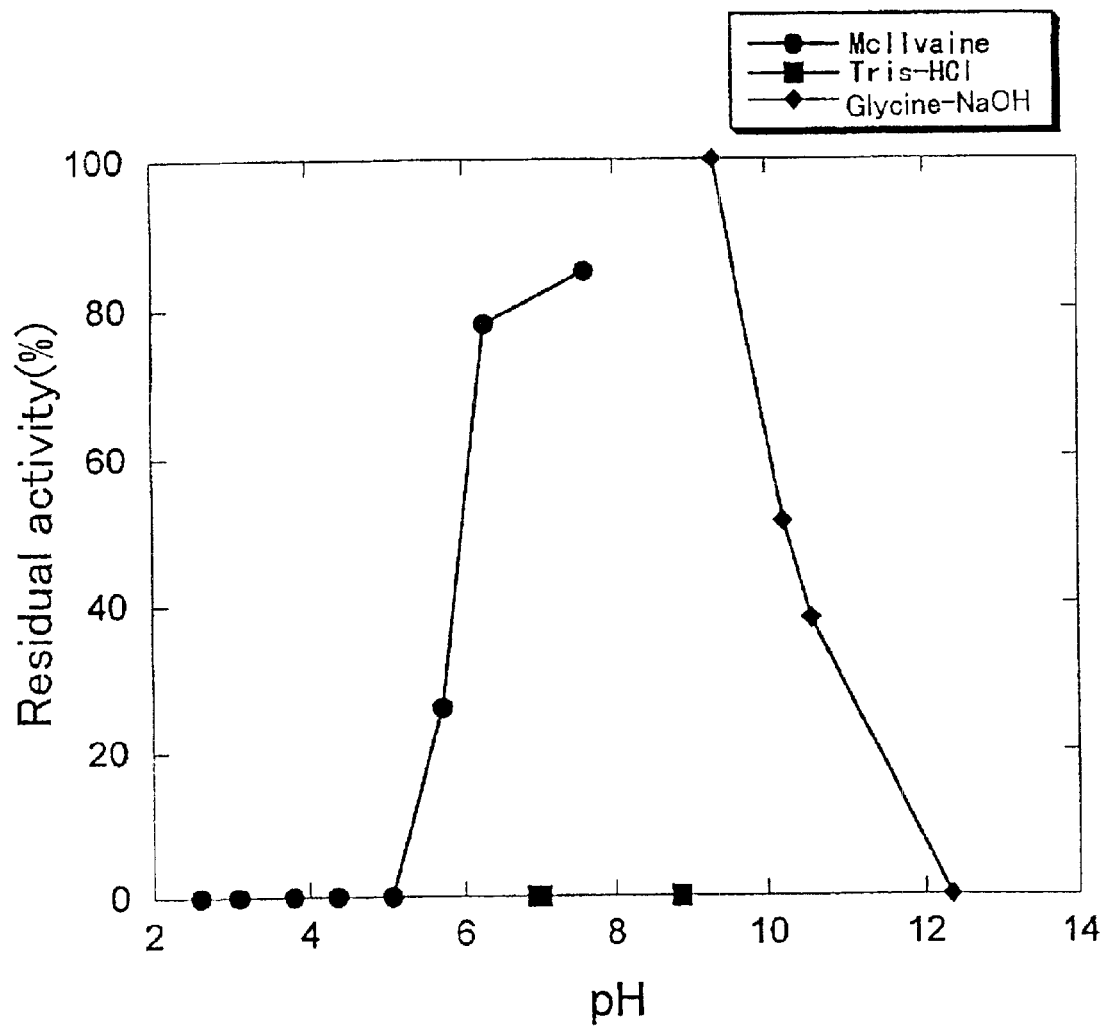
FIG. 4 is a diagram showing a result of measurement to determine the pH stability of (R)-2,3-butanediol dehydrogenase. The activity is represented by a residual activity when the activity of untreated sample is taken as 100.

The enzyme obtained in Example 1 was incubated in each of McIlvaine buffer, Tris-HCl buffer and glycine-NaOH buffer at pH 2 to 12 at 30° C. for 10 minutes to assay the residual activity. The result was represented by a residual activity, taking the residual activity of untreated enzyme as 100, and is shown in FIG. 4. The (R)-2,3-butanediol dehydrogenase of the present invention was relatively stable at pH 6 to 9.5.

EXAMPLE 6

Thermal stability of (R)-2,3-butanediol dehydrogenase

Figure 5:
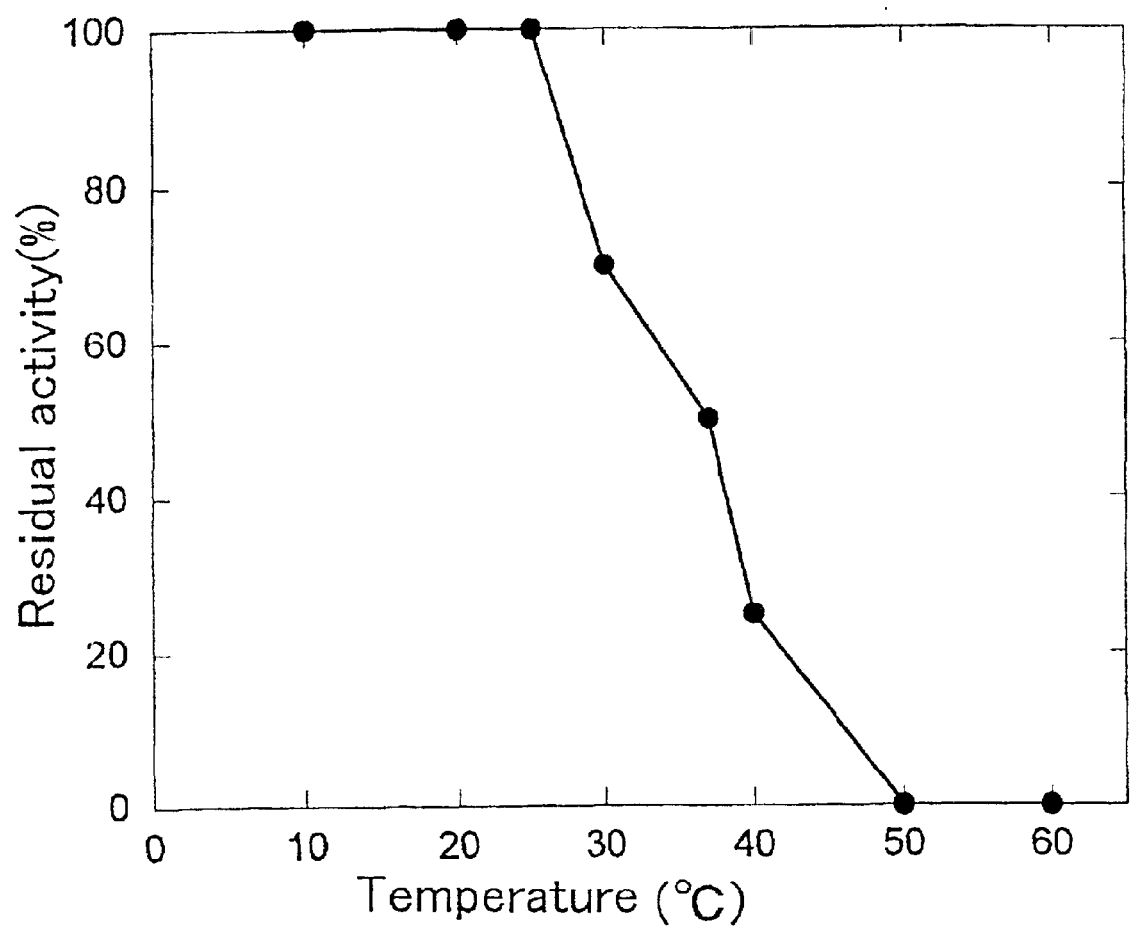
FIG. 5 is a diagram showing a result of measurement to determine the thermal stability of (R)-2,3-butanediol dehydrogenase. The activity is represented by a residual activity when the activity of untreated enzyme is taken as 100.

The enzyme obtained in Example 1 was allowed to stand at pH 7.5 for 10 minutes, and then glycerol dehydrogenase activity was assayed. The result was represented by a residual activity, taking the residual activity of untreated enzyme as 100, and is shown in FIG. 5. The (R)-2,3-butanediol dehydrogenase of the present invention was relatively stable up to 30° C.

EXAMPLE 7

Substrate specificity of (R)-2,3-butanediol dehydrogenase

The enzyme obtained in Example 1 was allowed to react with various reagents of 500 mM, and then the dehydrogenation activity was assayed. The result was represented by a relative activity, taking, as 100, glycerol dehydrogenation activity whose coenzyme was $NAD^+$, and is shown in Table 2.

TABLE 2

| Substrate | Relative activity (%) |
| --- | --- |
| Glycerol | 100 |
| 1,2-propanediol | 700 |
| 1,3-propanediol | ND |
| Ethanol | ND |
| 1-propanol | ND |
| 2-propanol | ND |
| Propionic acid | ND |
| 1,2-butanediol | 130 |
| 1,3-butanediol | 58 |
| 1,4-butanediol | ND |
| 2,3-butanediol | 3030 |

ND: not detectable

EXAMPLE 8

Stereoselectivity of (R)-2,3-butanediol dehydrogenase

The enzyme obtained in Example 1 was allowed to react with each of the two isomers 1,2-propanediol and 2,3-butanediol (500 mM each). The activity was represented by a relative activity when the activity to glycerol was taken as 100, which is shown in Table 3.

TABLE 3

| Substrate Relative activity | (%) |
| --- | --- |
| Glycerol | 100 |
| (R)-1,2-propanediol | 2000 |
| (S)-1,2-propanediol | 400 |
| (R)-2,3-propanediol | 6100 |
| (S)-2,3-propanediol | 160 |

EXAMPLE 9

Behavior of (R)-2,3-butanediol dehydrogenase to reagents

After treated with various reagents at 30° C. for 10 minutes, glycerol dehydrogenase activity was assayed. The activity was represented by a residual activity, taking the residual activity after the treatment at 30° C. for 10 minutes as 100, and is shown in Table 4. The (R)-2,3-butanediol dehydrogenase of the present invention was markedly inhibited by p-chloromercuribenzoic acid (PCMB), o-phenanthroline, 2,2'-dipyridyl, copper chloride, mercury chloride, iron (III) chloride and not by ethylenediaminetetraacetic acid (EDTA).

TABLE 4

| Reagent | Concentration (mM) | Residual activity (%) |
|---|---|---|
| — | — | 100 |
| 2,2'-dipyridyl | 1 | 0 |
| o-phenanthroline | 1 | 0 |
| EDTA | 1 | 93 |
| potassium cyanide | 1 | 89 |
| sodium azide | 1 | 99 |
| iodoacetic acid | 1 | 91 |
| PCMB | 0.1 | 0 |
| DTNB | 1 | 59 |
| Phenylhydrazine | 1 | 110 |
| lithium chloride | 1 | 101 |
| magnesium chloride | 1 | 105 |
| calcium chloride | 1 | 105 |
| manganese chloride | 1 | 105 |
| cobalt chloride | 1 | 102 |
| nickel chloride | 1 | 99 |
| copper chloride | 1 | 0 |
| zinc chloride | 1 | 113 |
| barium chloride | 1 | 112 |
| mercury chloride | 1 | 0 |
| iron (II) chloride | 1 | 163 |
| iron (III) chloride | 1 | 0 |

DTNB: 5,5'-dithiobis (2-nitrobenzoic acid)

EXAMPLE 10

Partial amino acid sequence of (R)-2,3-butanediol dehydrogenase

The N-terminal amino acid sequence of the enzyme obtained in Example 1 was analyzed with a protein sequencer; the result suggested that the N terminal amino acid had been blocked. Then, the purified enzyme was partially digested with V8 protease (Sigma) and separated by SDS-PAGE. The protein was blotted onto a PVDF membrane.

The amino acid sequences of the blotted peptide fragments were analyzed by a protein sequencer (Applied Biosystems), which resulted in three different amino acid sequences. The amino acid sequences of peptide A, peptide B, and peptide C are shown in SEQ ID NO:3, SEQ ID NO:4, and SEQ ID NO:5, respectively.

SEQ ID NO:3—peptide A
  Lys-Pro-Gly-Asp-Arg-Val-Ala-Val-Glu-Ala
SEQ ID NO:4—peptide B
  Ala-Thr-Ser-His-Cys-Ser-Asp-Arg-Ser-Arg-Tyr-Lys-Asp-Thr-Val-Ala-Gln-Asp-Leu-Gly-Leu
SEQ ID NO:5—peptide C p Phe-His-Ala-Ala-Phe-Asp

EXAMPLE 11

Preparation of chromosomal DNA from *Pichia angusta*

Chromosome DNA was purified from *Pichia angusta* ATCC 26012 strain according to a method of Cryer et al. (Meth. Cell Biol., 12:39–44, 1975).

EXAMPLE 12

Cloning of core region of the (R)-2,3-butanediol dehydrogenase gene by PCR

A sense primer A corresponding to peptide A and an antisense primer C corresponding to peptide C were synthesized. The respective nucleotide sequences are shown in SEQ ID NO:6 (primer A), and SEQ ID NO:7 (primer C).

primer A (SEQ ID NO:6)
AARCCNGGNGAYMGNGTNGC
primer C (SEQ ID NO:7)
TCRTCRAANGCNGCRTGRAA

EXAMPLE 13

PCR Conditions

30 μL of a bottom-layer reaction mixture containing *Pichia angusta*-derived chromosomal DNA (200 ng), ExTaq (1.25 U), and a buffer for ExTaq (TaKaRa) were treated at 80° C. for 5 minutes and then at 4° C. for 1 minute, and then 20 μL of a top-layer reaction mixture containing primers A and B (20 pmol each), dNTP (20 nmol) and the buffer for ExTaq were added onto AmpliWaxPCR Gem 50 (TaKaRa). The mixture was heat-treated at 94° C. for one minute and further was subjected to thermal cycling with 35 cycles at 94° C. for 1 minute, at 56° C. for 1 minute, and then at 72° C. for 2 minutes.

EXAMPLE 14

Subcloning of PCR fragment from core region of the (R)-2,3-butanediol dehydrogenase gene The DNA fragment obtained in Example 13 was purified by electrophoresis with 1% low-melting agarose. The purified DNA fragment was ligated with vector pT7Blue-2T (TaKaRa) by using a Takara Ligation Kit; *E. coli* JM109 strain was transformed with the resulting DNA construct; the transformants were grown on a plate with LB medium (1% bacto-tryptone, 0.5% bacto-yeast extract, 1% sodium chloride; hereinafter abbreviated to LB medium) containing ampicillin (50 μg/ml).

Plasmid was purified from a transformed strain having the plasmid of interest, and then nucleotide sequence of the inserted DNA was analyzed. PCR was performed with a Big-Dye Terminator Cycle Sequencing ready Reaction Kit (Applied BioSystems), and then the nucleotide sequence of the DNA was analyzed in a PRISM 310 Genetic Analyzer (Applied BioSystems). The determined nucleotide sequence of core region is shown in SEQ ID NO:8.

EXAMPLE 15

Subcloning of DNA regions adjacent to the core region of the (R)-2,3-butanediol dehydrogenase gene

*Pichia angusta*-derived chromosomal DNA was digested with each of restriction enzymes ApoI, PstI and XhoI, and then self-ligated at 16° C. overnight by using T4 ligase to cyclize each fragment. Subsequently PCR was performed in 50 μL of a reaction mixture containing primer PODR-C5U (50 pmol; SEQ ID NO:9), PODR-C3D (50 pmol; SEQ ID NO:10), dNTP (10 nmol), the self-ligated DNA (50 ng), the buffer for Ex-Taq (TaKaRa), and Ex-Taq (1.5 U) (TaKaRa) with 30 cycles of denaturation (94° C. for 30 seconds), annealing (55° C. for 30 seconds), and extension (72° C. for 6 minutes and 40 seconds) by using a GeneAmp PCR System 2400 (Perkin Elmer). An aliquot of the PCR mixture was analyzed by agarose gel electrophoresis, and the result showed that DNA fragments of about 760 bp, 6000 bp and 3500 bp were detectable corresponding to the template DNA digested with ApoI, PstI or XhoI, respectively.

PODR-C5U (SEQ ID NO: 9)
TTGGCATGCGATCTGTCGGAGCAATG
PODR-C3D (SEQ ID NO: 10)
TGAGCATGCAAATGCTGTTCTCAAGGC

Each DNA fragment amplified by PCR was recovered by ethanol precipitation after phenol/chloroform extraction. Then the DNA was digested with restriction enzyme SphI and then electrophoresed in an agarose gel; the band of interest was cut out (because there was a SphI cleavage site in the PCR-amplified fragment obtained from the DNA digested with XhoI and PstI as a template, the PCR fragment was separated to two fragments. Of the two, the larger DNA fragment was purified) and then the DNA was purified and recovered with Sephaglas (provided by Pharmacia).

Each of the resulting DNA fragments was ligated with pUC18 (TaKaRa that had been digested with restriction enzyme SphI), by using a Takara Ligation Kit Ver.2; *E. coli* JM109 strain was transformed with the ligated DNA. The transformed strain was grown on a plate of LB medium containing ampicillin (50 µg/mL), 5-bromo-4-chloro-3-indolyl-β-D-galactopyranoside (50 µg/mL), and isopropylthio-b-D-galactopyranoside (hereinafter designated as IPTG) (20 µg/mL); some white colonies were cultured in liquid LB medium containing ampicillin and then the plasmids were purified with Flexi-Prep (provided by Pharmacia). The resulting plasmids were named pPAD-Apo, pPAD-Pst, and pPAD-Xho, which, respectively, correspond to restriction enzymes ApoI, PstI and XhoI that were used for the preparation of DNA as PCR templates.

The nucleotide sequences of inserted DNAs were analyzed by using the purified plasmids. Nucleotide sequence analysis of the DNAs was carried out by PCR using a Dye Terminator Cycle Sequencing FS ready Reaction Kit (Perkin Elmer) in a DNA sequencer 373A (Perkin Elmer).

The determined nucleotide sequences of inserted DNA fragments in pPAD-Apo, pPAD-Pst and pPAD-Xho were divided into the core region, 5'-unpstream (5U) and 3'-downstream (3D) regions, and the respective sequences are shown as Apo-5U (SEQ ID NO:11), Apo-3D (SEQ ID NO: 12), and Pst-5U (SEQ ID NO:13). Further, the positions of these DNA fragments are indicated in a restriction enzyme map of FIG. 6.

Because there was an SphI cleavage site in the PCR-amplified fragment, a fragment was not cloned between the upstream ApoI and the SphI site. Then, by using newly synthesized primer PODR-SPH (SEQ ID NO:14) together with primer PODR-C5U, PCR was carried out with chromosomal DNA purified from *Pichia angusta* as a template; the resulting PCR product was purified, and then digested with PstI. The digestion product was ligated with PstI-SmaI double-digested pUC18 to obtain plasmid pPAD-Sph. The nucleotide sequence of inserted partial fragment in pPAD-Sph was determined and it is shown as Sph-5U in SEQ ID NO:15.

Figure 6:
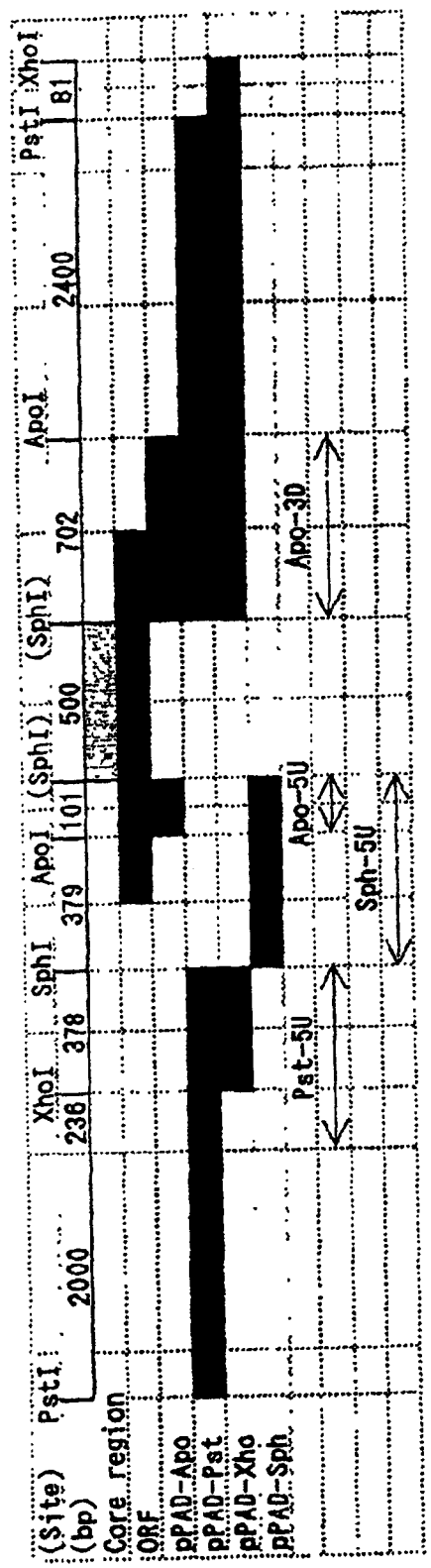
FIG. 6 is a diagram showing a restriction enzyme map of a region around the (R)-2,3-butanediol dehydrogenase gene.

The respective nucleotide sequences of Pst-5U, Sph-5U, Apo-5U and Apo-3D were synthesized based on the map in FIG. 6, and then the sequence of the (R)-2,3-butanediol dehydrogenase gene was determined by open reading frame (ORF) search. The determined DNA sequence is shown in SEQ ID NO:1; the sequence encoding the protein is shown in SEQ ID NO:2. The design and ORF search were performed by Genetyx-ATSQ/WIN and Genetyx-WIN programs (both are from Software Development Co).

EXAMPLE 16

Cloning of the (R)-2,3-butanediol dehydrogenase gene

Primers PAD-ATG1 (SEQ ID NO:16) and PAD-TAA1 (SEQ ID NO:17) to be used for the construction of expression vector were synthesized based on the nucleotide sequence of structural gene for (R)-2,3-butanediol dehydrogenase. PCR was carried out by using 50 µL of a reaction mixture containing each primer (50 pmol each), dNTP (10 nmol), *Pichia angusta*-derived chromosomal DNA (50 ng), a buffer for Pfu-DNA polymerase (STRATAGENE) and Pfu-DNA polymerase (2 U; STRATAGENE) with 30 cycles of denaturation (95° C. for 30 seconds), annealing (50° C. for 1 minute), extension (75° C. for 5 minutes) in a Gene-Amp PCR System 2400 (Perkin Elmer).

PAD-ATG1 (SEQ ID NO:16)
TGCTCATGAAAGGTTTACTTTATTACGGTA
PAD-TAA1 (SEQ ID NO:17)
CAGTCTAGATTAGGAAACCTCGTTCGGC

An aliquot of the PCR reaction mixture was analyzed by agarose gel electrophoresis, and a specific band was detectable.

After phenol/chloroform extraction, the resulting DNA fragment was recovered by ethanol precipitation. The DNA fragment was double-digested with restriction enzymes BspHI and XbaI and the DNA was electrophoresed on an agarose gel; a portion containing a band of interest was cut out and the DNA was purified with Sephaglas (provided by Pharmacia).

The resulting DNA fragment was ligated with NcoI-XbaI double-digested pSE420D (a plasmid which was obtained by modifying the multi-cloning site of plasmid vector pSE420 from Invitrogen; unexamined published Japanese patent application No. 2000-189170) by using a Takara Ligation Kit, and *E. coli* HB101 strain was transformed with this DNA.

The transformed strain was grown on a plate of LB medium containing ampicillin (50 µg/ml), and plasmids were purified from some colonies of them; the nucleotide sequences of inserted fragments were analyzed. A plasmid of interest, which contains the (R)-2,3-butanediol dehydrogenase gene, was named pSE-PAD1.

EXAMPLE 17

Production of recombinant (R)-2,3-butanediol dehydrogenase in *E. coli*

*E. coli* HB101 strain transformed with expression plasmid pSE-PAD1 for the (R)-2,3-butanediol dehydrogenase gene was cultured in liquid LB medium containing ampicillin at 30° C. overnight, and then 0.1 mM IPTG (isopropylthiogalactoside) was added thereto; the cultivation was further continued for 4 hours.

The bacterial cells were collected by centrifugal separation and then suspended in 100 mM potassium phosphate buffer (pH 8.0) containing 0.02% 2-mercaptoethanol; the bacterial cells were lysed by the treatment with a closed sonic chamber device UCD-200TM (Cosmo Bio) for 4 minutes. The bacterial cell lysate was separated by centrifugation and the resulting supernatant was recovered as a bacterial cell extract.

EXAMPLE 18

Substrate specificity of recombinant (R)-2,3-butanediol dehydrogenase

The activity of recombinant (R)-2,3-butanediol dehydrogenase prepared in Example 17 was assayed by using various substrates; the result was compared with the activity of cell-free extract prepared in the absence of plasmid in the same manner as in Example 17. The result of oxidation reaction is shown in Table 5 and the result of reduction reaction was in Table 6.

TABLE 5

| | | Host only | HB101 (pSE-PAD1) | |
|---|---|---|---|---|
| Substrate | mM | U/mg | U/mg | Relative activity |
| Glycerol | 100 | 0 | 0.228 | 100% |
| (R)-1,2-propanediol | 50 | 0 | 1.077 | 473% |
| (S)-1,2-propanediol | 50 | 0 | 0.246 | 108% |
| (R)-3-chloro-1,2-propanediol | 50 | 0 | 0.002 | 0.9% |
| (S)-3-chloro-1,2-propanediol | 50 | 0.001 | 0.057 | 24.8% |
| (RS)-1,2-butanediol | 100 | 0.002 | 0.200 | 87.6% |
| (R)-1,3-butanediol | 50 | 0 | 0.259 | 114% |
| (S)-1,3-butanediol | 50 | 0 | 0.042 | 18.3% |
| (2R,3R)-2,3-butanediol | 50 | 0 | 1.414 | 620% |

TABLE 5-continued

| | | Host only | HB101 (pSE-PAD1) | |
|---|---|---|---|---|
| Substrate | mM | U/mg | U/mg | Relative activity |
| (2S,3S)-2,3-butanediol | 50 | 0 | 0.059 | 26.1% |
| Meso-2,3-butanediol | 50 | 0 | 1.163 | 509% |
| 3-hydroxy-2-butanone | 50 | 0.006 | 0.020 | 8.8% |
| (R)-2-butanol | 50 | 0 | 0.022 | 9.6% |
| (S)-2-butanol | 50 | 0 | 0.024 | 10.7% |
| (R)-1-amino-2-propanol | 50 | 0.007 | 0.051 | 22.2% |
| (S)-1-amino-2-propanol | 50 | 0.007 | 0.018 | 8.0% |
| (RS)-2-amino-1-propanol | 50 | 0.002 | 0.008 | 3.6% |

TABLE 6

| | | Host only | HB101 (pSE-PAD1) | |
|---|---|---|---|---|
| Substrate | mM | U/mg | U/mg | Relative activity |
| Dihydroxyacetone | 20 | 0.010 | 0.979 | 100% |
| Hydroxyacetone | 20 | 0 | 0.364 | 37.2% |
| 2-butanone | 20 | 0.002 | 0.008 | 0.8% |
| 3-hydroxy-2-butanone | 20 | 0.009 | 0.696 | 71.2% |
| 2,3-butanedion | 20 | 0.018 | 1.906 | 195% |
| 4-hydroxy-2-butanone | 20 | 0.006 | 0.011 | 1.1% |

What is claimed is:

1. An isolated polypeptide the amino acid sequence of which comprises a sequence at least 95% percent identical to the amino acid sequence of SEQ ID NO: 2, wherein the polypeptide is a (R)-2,3-butanediol dehydrogenase that:
    (a) produces (R)-acetoin by acting on (2R,3R)-2,3-butanediol using nicotinamide adenine dinucleotide as a coenzyme and produces (2R,3R)-2,3-butanediol by reducing 2,3-butanedione using a reduced form of nicotinamide adenine dinucleotide as a coenzyme;
    (b) uses nicotinamide adenine dinucleotide as a coenzyme in an oxidation reaction;
    (c) uses a reduced form of nicotinamide adenine dinucleotide as a coenzyme in a reduction reaction; and
    (d) preferentially oxidizes a hydroxyl group of 2,3-butanediol in (R) configuration.

2. An isolated polypeptide encoded by a polynucleotide that is at least 95% identical to a polynucleotide comprising the nucleotide sequence of SEQ ID NO: 1, wherein the polypeptide is a (R)-2,3-butanediol dehydrogenase that:
    (a) produces (R)-acetoin by acting on (2R,3R)-2,3-butanediol using nicotinamide adenine dinucleotide as a coenzyme and produces (2R,3R)-2,3-butanediol by reducing 2,3-butanedione using a reduced form of nicotinamide adenine dinucleotide as a coenzyme;
    (b) uses nicotinamide adenine dinucleotide as a coenzyme in an oxidation reaction;
    (c) uses a reduced form of nicotinamide adenine dinucleotide as a coenzyme in a reduction reaction; and
    (d) preferentially oxidizes a hydroxyl group of 2,3-butanediol in (R) configuration.

3. An isolated polypeptide, wherein the polypeptide is an (R)-2,3-butanediol dehydrogenase that:
    (a) produces (R)-acetoin by acting on (2R,3R)-2,3-butanediol using nicotinamide adenine dinucleotide as a coenzyme and produces (2R,3R)-2,3-butanediol by reducing 2,3-butanedione using a reduced form of nicotinamide adenine dinucleotide as a coenzyme;
    (b) uses nicotinamide adenine dinucleotide as a coenzyme in an oxidation reaction;
    (c) uses a reduced form of nicotinamide adenine dinucleotide as a coenzyme in a reduction reaction;
    (d) preferentially oxidizes a hydroxyl group of 2,3-butanediol in (R) configuration;
    (e) has a specific activity of about 100 U/mg or higher when purified;
    (f) has an optimal pH of 10 for a glycerol oxidation reaction;
    (g) has a molecular weight of about 36,000 Da when determined by sodium dodecyl sulfate-polyacrylamide gel electrophoresis and about 76,000 Da when determined by gel filtration, and
    (h) has the sequence of an enzyme naturally produced by *Pichia angusta*.

4. An isolated polypeptide the amino acid sequence of which consists of SEQ ID NO:2.

5. An isolated polypeptide the amino acid sequence of which comprises SEQ ID NO:2.

6. An isolated polypeptide the amino acid sequence of which comprises SEQ ID NO:2 with 0 to 10 conservative amino acid substitutions, wherein the polypeptide is a (R)-2,3-butanediol dehydrogenase.

7. A substantially pure polypeptide, the amino acid sequence of which comprises a sequence at least 95% percent identical to the amino acid sequence of SEQ ID NO: 2, wherein the polypeptide is a (R)-2,3-butanediol dehydrogenase that:
    (a) produces (R)-acetoin by acting on (2R,3R)-2,3-butanediol using nicotinamide adenine dinucleotide as a coenzyme and produces (2R,3R)-2,3-butanediol by reducing 2,3-butanedione using a reduced form of nicotinamide adenine dinucleotide as a coenzyme;
    (b) uses nicotinamide adenine dinucleotide as a coenzyme in an oxidation reaction;
    (c) uses a reduced form of nicotinamide adenine dinucleotide as a coenzyme in a reduction reaction; and (d) preferentially oxidizes a hydroxyl group of 2,3-butanediol in (R) configuration.

8. A substantially pure polypeptide encoded by a polynucleotide that is at least 95% identical to a polynucleotide comprising the nucleotide sequence of SEQ ID NO: 1, wherein the polypeptide is a (R)-2,3-butanediol dehydrogenase that:

(a) produces (R)-acetoin by acting on (2R,3R)-2,3-butanediol using nicotinamide adenine dinucleotide as a coenzyme and produces (2R,3R)-2,3-butanediol by reducing 2,3-butanedione using a reduced form of nicotinamide adenine dinucleotide as a coenzyme;

(b) uses nicotinamide adenine dinucleotide as a coenzyme in an oxidation reaction;

(c) uses a reduced form of nicotinamide adenine dinucleotide as a coenzyme in a reduction reaction; and (d) preferentially oxidizes a hydroxyl group of 2,3-butanediol in (R) configuration.

9. A substantially pure polypeptide, wherein the polypeptide is an (R)-2,3-butanediol dehydrogenase that:

(a) produces (R)-acetoin by acting on (2R,3R)-2,3-butanediol using nicotinamide adenine dinucleotide as a coenzyme and produces (2R,3R)-2,3-butanediol by reducing 2,3-butanedione using a reduced form of nicotinamide adenine dinucleotide as a coenzyme;

(b) uses nicotinamide adenine dinucleotide as a coenzyme in an oxidation reaction;

(c) uses a reduced form of nicotinamide adenine dinucleotide as a coenzyme in a reduction reaction;

(d) preferentially oxidizes a hydroxyl group of 2,3-butanediol in (R) configuration;

(e) has a specific activity of about 100 U/mg or higher when purified;

(f) has an optimal pH of 10 for a glycerol oxidation reaction;

(g) has a molecular weight of about 36,000 Da when determined by sodium dodecyl sulfate-polyacrylamide gel electrophoresis and about 76,000 Da when determined by gel filtration, and (h) has the sequence of an enzyme naturally produced by *Pichia angusta*.

10. A substantially pure polypeptide, the amino acid sequence of which consists of SEQ ID NO:2.

11. A substantially pure polypeptide, the amino acid sequence of which comprises SEQ ID NO:2.

12. A substantially pure polypeptide, the amino acid sequence of which comprises SEQ ID NO:2 with 0 to 10 conservative amino acid substitutions, wherein the polypeptide is a (R)-2,3-butanediol dehydrogenase.

13. A method for producing an alcohol, the method comprising
reacting the isolated polypeptide of claim 1 with a ketone in the presence of a reduced form of nicotinamide adenine dinucleotide to generate an alcohol, and
recovering the generated alcohol.

14. A method for producing an alcohol, the method comprising
reacting the isolated polypeptide of claim 2 with a ketone in the presence of a reduced form of nicotinamide adenine dinucleotide to generate an alcohol, and
recovering the generated alcohol.

15. A method for producing an alcohol, the method comprising
reacting the isolated polypeptide of claim 3 with a ketone in the presence of a reduced form of nicotinamide adenine dinucleotide to generate an alcohol, and
recovering the generated alcohol.

16. A method for producing an alcohol, the method comprising
reacting the isolated polypeptide of claim 4 with a ketone in the presence of a reduced form of nicotinamide adenine dinucleotide to generate an alcohol, and
recovering the generated alcohol.

17. A method for producing an alcohol, the method comprising
reacting the isolated polypeptide of claim 5 with a ketone in the presence of a reduced form of nicotinamide adenine dinucleotide to generate an alcohol, and
recovering the generated alcohol.

18. A method for producing an alcohol, the method comprising
reacting the isolated polypeptide of claim 6 with a ketone in the presence of a reduced form of nicotinamide adenine dinucleotide to generate an alcohol, and
recovering the generated alcohol.

19. A method for producing an alcohol, the method comprising
reacting the substantially pure polypeptide of claim 7 with a ketone in the presence of a reduced form of nicotinamide adenine dinucleotide to generate an alcohol, and
recovering the generated alcohol.

20. A method for producing an alcohol, the method comprising
reacting the substantially pure polypeptide of claim 8 with a ketone in the presence of a reduced form of nicotinamide adenine dinucleotide to generate an alcohol, and
recovering the generated alcohol.

21. A method for producing an alcohol, the method comprising
reacting the substantially pure polypeptide of claim 9 with a ketone in the presence of a reduced form of nicotinamide adenine dinucleotide to generate an alcohol, and
recovering the generated alcohol.

22. A method for producing an alcohol, the method comprising
reacting the substantially pure polypeptide of claim 10 with a ketone in the presence of a reduced form of nicotinamide adenine dinucleotide to generate an alcohol, and
recovering the generated alcohol.

23. A method for producing an alcohol, the method comprising
reacting the substantially pure polypeptide of claim 11 with a ketone in the presence of a reduced form of nicotinamide adenine dinucleotide to generate an alcohol, and
recovering the generated alcohol.

24. A method for producing an alcohol, the method comprising
reacting the substantially pure polypeptide of claim 12 with a ketone in the presence of a reduced form of nicotinamide adenine dinucleotide to generate an alcohol, and
recovering the generated alcohol.

25. The method of claim 13, wherein the ketone is 2,3-butanedione and the alcohol is (2R,3R)-2,3-butanediol.

26. The method of claim 14, wherein the ketone is 2,3-butanedione and the alcohol is (2R,3R)-2,3-butanediol.

27. The method of claim 15, wherein the ketone is 2,3-butanedione and the alcohol is (2R,3R)-2,3-butanediol.

28. The method of claim 16, wherein the ketone is 2,3-butanedione and the alcohol is (2R,3R)-2,3-butanediol.

29. The method of claim 17, wherein the ketone is 2,3-butanedione and the alcohol is (2R,3R)-2,3-butanediol.

30. The method of claim 18, wherein the ketone is 2,3-butanedione and the alcohol is (2R,3R)-2,3-butanediol.

31. The method of claim 19, wherein the ketone is 2,3-butanedione and the alcohol is (2R,3R)-2,3-butanediol.

32. The method of claim 20, wherein the ketone is 2,3-butanedione and the alcohol is (2R,3R)-2,3-butanediol.

33. The method of claim 21, wherein the ketone is 2,3-butanedione and the alcohol is (2R,3R)-2,3-butanediol.

34. The method of claim 22, wherein the ketone is 2,3-butanedione and the alcohol is (2R,3R)-2,3-butanediol.

35. The method of claim 23, wherein the ketone is 2,3-butanedione and the alcohol is (2R,3R)-2,3-butanediol.

36. The method of claim 24, wherein the ketone is 2,3-butanedione and the alcohol is (2R,3R)-2,3-butanediol.

* * * * *

SEQUENCE LISTING

<160> NUMBER OF SEQ ID NOS: 17

<210> SEQ ID NO 1
<211> LENGTH: 1143
<212> TYPE: DNA
<213> ORGANISM: Pichia angusta

<400> SEQUENCE: 1

```
atgaaaggtt tactttatta cggtacaaac gatattcgct actccgaaac ggttcctgaa      60
ccggagatca agaatcccaa cgatgtcaag atcaaagtca gctattgtgg aatctgtggc     120
acggacttga agaattcac atattctgga ggtcctgttt ttttccctaa acaaggcacc      180
aaggacaaga tttcgggata cgaacttcct ctctgtcctg gacatgaatt tagcggaacg     240
gtggtcgagg ttggctctgg tgtcacaagt gtgaaacctg gtgacagagt cgcagttgaa     300
gctacgtcgc attgctccga cagatcgcgc tacaaggaca cggtcgccca agaccttggg     360
ctctgtatgg cctgccagag cggatctccg aactgctgtg cgtcgctgag cttctgcggt     420
ttgggtggtg ccagcggcgg ttttgccgag tacgtcgttt acggtgagga ccacatggtc     480
aagctgccag actcgattcc cgacgatatt ggagcactgg ttgagcctat ttctgttgcc     540
tggcatgctg ttgaacgcgc tagattccag cctggtcaga cggccctggt tcttggagga     600
ggtcctatcg gccttgccac cattcttgct ctgcaaggcc atcatgcggg caaaattgtg     660
tgttccgagc cggccttgat cagaagacag tttgcaaagg aactgggcgc tgaagtgttc     720
gatccttcta catgtgacga cgcaaatgct gttctcaagg ctatggtgcc ggagaacgag     780
ggattccatg cagccttcga ctgctctggt gttcctcaga cattcaccac ctcaattgtc     840
```

```
gccacgggac cttctggaat cgccgtcaat gtggccgttt ggggagacca cccaattgga      900
ttcatgccaa tgtctctgac ttaccaggag aaatacgcta ccggctccat gtgctacacc      960
gtcaaggact tccaggaagt tgtcaaggcc ttggaagatg gtctcatatc tttggacaaa     1020
gcgcgcaaga tgattacagg caaagtccac ctaaaggacg agtcgagaa gggctttaaa      1080 cagctgatcg agcacaagga gaacaatgtc aagatcctgg tgacgccgaa cgaggtttcc     1140
taa                                                                   1143
```

<210> SEQ ID NO 2
<211> LENGTH: 380
<212> TYPE: PRT
<213> ORGANISM: Pichia angusta

<400> SEQUENCE: 2

```
Met Lys Gly Leu Leu Tyr Tyr Gly Thr Asn Asp Ile Arg Tyr Ser Glu
 1               5                  10                  15

Thr Val Pro Glu Pro Glu Ile Lys Asn Pro Asn Asp Val Lys Ile Lys
            20                  25                  30

Val Ser Tyr Cys Gly Ile Cys Gly Thr Asp Leu Lys Glu Phe Thr Tyr
        35                  40                  45

Ser Gly Gly Pro Val Phe Phe Pro Lys Gln Gly Thr Lys Asp Lys Ile
    50                  55                  60

Ser Gly Tyr Glu Leu Pro Leu Cys Pro Gly His Glu Phe Ser Gly Thr
65                  70                  75                  80

Val Val Glu Val Gly Ser Gly Val Thr Ser Val Lys Pro Gly Asp Arg
                85                  90                  95

Val Ala Val Glu Ala Thr Ser His Cys Ser Asp Arg Ser Arg Tyr Lys
           100                 105                 110

Asp Thr Val Ala Gln Asp Leu Gly Leu Cys Met Ala Cys Gln Ser Gly
       115                 120                 125

Ser Pro Asn Cys Cys Ala Ser Leu Ser Phe Cys Gly Leu Gly Gly Ala
   130                 135                 140

Ser Gly Gly Phe Ala Glu Tyr Val Val Tyr Gly Glu Asp His Met Val
145                 150                 155                 160

Lys Leu Pro Asp Ser Ile Pro Asp Ile Gly Ala Leu Val Glu Pro
               165                 170                 175

Ile Ser Val Ala Trp His Ala Val Glu Arg Ala Arg Phe Gln Pro Gly
           180                 185                 190

Gln Thr Ala Leu Val Leu Gly Gly Pro Ile Gly Leu Ala Thr Ile
       195                 200                 205

Leu Ala Leu Gln Gly His His Ala Gly Lys Ile Val Cys Ser Glu Pro
   210                 215                 220

Ala Leu Ile Arg Arg Gln Phe Ala Lys Glu Leu Gly Ala Glu Val Phe
225                 230                 235                 240

Asp Pro Ser Thr Cys Asp Asp Ala Asn Ala Val Leu Lys Ala Met Val
               245                 250                 255

Pro Glu Asn Glu Gly Phe His Ala Ala Phe Asp Cys Ser Gly Val Pro
           260                 265                 270

Gln Thr Phe Thr Thr Ser Ile Val Ala Thr Gly Pro Ser Gly Ile Ala
       275                 280                 285

Val Asn Val Ala Val Trp Gly Asp His Pro Ile Gly Phe Met Pro Met
   290                 295                 300

Ser Leu Thr Tyr Gln Glu Lys Tyr Ala Thr Gly Ser Met Cys Tyr Thr
305                 310                 315                 320
```

```
Val Lys Asp Phe Gln Glu Val Val Lys Ala Leu Glu Asp Gly Leu Ile
            325                 330                 335

Ser Leu Asp Lys Ala Arg Lys Met Ile Thr Gly Lys Val His Leu Lys
            340                 345                 350

Asp Gly Val Glu Lys Gly Phe Lys Gln Leu Ile Glu His Lys Glu Asn
            355                 360                 365

Asn Val Lys Ile Leu Val Thr Pro Asn Glu Val Ser
            370                 375                 380

<210> SEQ ID NO 3
<211> LENGTH: 10
<212> TYPE: PRT
<213> ORGANISM: Pichia angusta

<400> SEQUENCE: 3

Lys Pro Gly Asp Arg Val Ala Val Glu Ala
1               5                   10

<210> SEQ ID NO 4
<211> LENGTH: 21
<212> TYPE: PRT
<213> ORGANISM: Pichia angusta

<400> SEQUENCE: 4

Ala Thr Ser His Cys Ser Asp Arg Ser Arg Tyr Lys Asp Thr Val Ala
1               5                   10                  15

Gln Asp Leu Gly Leu
            20

<210> SEQ ID NO 5
<211> LENGTH: 6
<212> TYPE: PRT
<213> ORGANISM: Pichia angusta

<400> SEQUENCE: 5

Phe His Ala Ala Phe Asp
1               5

<210> SEQ ID NO 6
<211> LENGTH: 20
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: misc_feature
<222> LOCATION: 6, 9, 15, 18
<223> OTHER INFORMATION: n = a, c, g, or t

<400> SEQUENCE: 6
aarccnggng aymgngtngc                                              20

<210> SEQ ID NO 7
<211> LENGTH: 20
<212> TYPE: DNA
<213> ORGANISM: Artificial Sequence
<220> FEATURE:
<223> OTHER INFORMATION: Artificially synthesized primer sequence
<220> FEATURE:
<221> NAME/KEY: misc_feature
<222> LOCATION: 9, 12
<223> OTHER INFORMATION: n = a, c, g, or t

<400> SEQUENCE: 7
```
tcrtcraang cngcrtgraa                                              20

<210> SEQ ID NO 8
<211> LENGTH: 530
<212> TYPE: DNA
<213> ORGANISM: Pichia angusta

<400> SEQUENCE: 8
aagccgggtg atcgtgtcgc agttgaagct acgtcgcatt gctccgacag atcgcgctac    60
aaggacacgg tcgcccaaga ccttgggctc tgtatggcct gccagagcgg atctccgaac   120
tgctgtgcgt cgctgagctt ctgcggtttg ggtggtgcca cgggcggttt tgccgagtac   180
gtcgtttacg gtgaggacca catggtcaag ctgccagact cgattcccga cgatattgga   240
gcactggttg agcctatttc tgttgcctgg catgctgttg aacgcgctag attccagcct   300
ggtcagacgg ccctggttct tggaggaggt cctatcggcc ttgccaccat tcttgctctg   360
caaggccatc atgcgggcaa aattgtgtgt ccgagccgg ccttgatcag aagacagttt    420
gcaaaggaac tgggcgctga agtgttcgat ccttctacat gtgacgacgc aaatgctgtt   480
ctcaaggcta tggtgccgga gaacgaggga ttccacgccg ccttcgatga              530

<210> SEQ ID NO 9
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 9
ttggcatgcg atctgtcgga gcaatg                                        26

<210> SEQ ID NO 10
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 10
tgagcatgca aatgctgttc tcaaggc                                       27

<210> SEQ ID NO 11
<211> LENGTH: 107
<212> TYPE: DNA
<213> ORGANISM: Pichia angusta

<400> SEQUENCE: 11
gaatttagcg gaacggtggt cgaggttggc tctggtgtca caagtgtgaa acctggtgac    60
agagtcgcag ttgaagctac gtcgcattgc tccgacagat cgcatgc                107

<210> SEQ ID NO 12
<211> LENGTH: 706
<212> TYPE: DNA
<213> ORGANISM: Pichia angusta

<400> SEQUENCE: 12
gcatgcaaat gctgttctca aggctatggt gccggagaac gagggattcc atgcagcctt    60
cgactgctct ggtgttcctc agacattcac cacctcaatt gtcgccacgg accttctgg   120 aatcgccgtc aatgtggccg tttggggaga ccacccaatt ggattcatgc caatgtctct   180
gacttaccag gagaaatacg ctaccggctc catgtgctac accgtcaagg acttccagga   240

```
agttgtcaag gccttggaag atggtctcat atctttggac aaagcgcgca agatgattac    300
aggcaaagtc cacctaaagg acggagtcga gaagggcttt aaacagctga tcgagcacaa    360
ggagaacaat gtcaagatcc tggtgacgcc aacgaggtt tcctaactaa taatatacat     420
acatcataca tatgtatgtc ctagagccaa gacttgcgca ttaggaaaaa tagctggtag    480
tttgcattat ggtggccggc ctcccaggaa attaatctat gatttacata tggactcgat    540
tacgtaacag gtgctgagca tttaataatt acctactatt ttctaaatta gtaaattgta    600
tgtttcttga gcaggaggag atactagagc aatttcaaaa catctccaat tgccaaatcc    660
ctgtgtccga acagattgca ttgctagagt ctgtgaactg gaattt                   706

<210> SEQ ID NO 13
<211> LENGTH: 620
<212> TYPE: DNA
<213> ORGANISM: Pichia angusta

<400> SEQUENCE: 13
tgacattcca caccaacttc tgccgccacc actgcaatcc tgtaggcgaa caggacgatg     60
caggactatt tctctatttt ttcccatcgt gcaccctgaa ccaatacggg ggaggcatgg    120
gaattttccg cgctaatcca gtcaacggta acaagaccag gatggagttt gaatatttct    180
ttgacggcag cgatgaggag ttcgaggcct acttcaagtt tgccagacag gtcgcactcg    240
aggatatttg gctgtgtgag gcggcccaac agaaccttat aagtggggtg taccaacagg    300
gcttgctgca tcctaaaaaa gaagtcgggg tggtttacta ccagtcgctg gttcgtgaaa    360
gaataatggc ttagctccga gatgtggagg cagtctggtc agactgtgcg gcaattaaat    420
aagacgcgga tgtactgcac cagagtgaat aaaggaattc caattcgata gcaaatattg    480
ctgtaataat gagtgaccag atttattacc gaacctagcc agcccggggt ttttacaca    540 ataggaaaaa aaggactcga ttattcgatg ctgctgcaaa tcacgccaga cataataagt    600
cacccgttta ctccgcatgc                                                620

<210> SEQ ID NO 14
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 14
tgcctgcagc gccagacata ataagtcacc                                      30

<210> SEQ ID NO 15
<211> LENGTH: 523
<212> TYPE: DNA
<213> ORGANISM: Pichia angusta

<400> SEQUENCE: 15
ctgcagcgcc agacataata agtcacccgt ttactccgca tgcactcccc cactgatcat     60
gattaatggt tctggacggc taaatcattg atcactgcgt cccggacctc gtaccgacgt    120
ggaaattagc cggcactcgg ttgtgagaga ttatcctata taaaccacaa aatcctatct    180
cccttttgcc aatgaaaggt ttactttatt acggtacaaa cgatattcgc tactccgaaa    240
cggttcctga accggagatc aagaatccca acgatgtcaa gatcaaagtc agctattgtg    300
gaatctgtgg cacggacttg aaagaattca catattctgg aggtcctgtt ttttccccta    360
```

```
aacaaggcac caaggacaag atttcgggat acgaacttcc tctctgtcct ggacatgaat      420
ttagcggaac ggtggtcgag gttggctctg gtgtcacaag tgtgaaacct ggtgacagag      480
tcgcagttga agctacgtcg cattgctccg acagatcgca tgc                        523

<210> SEQ ID NO 16
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 16
tgctcatgaa aggtttactt tattacggta                                        30

<210> SEQ ID NO 17
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 17
cagtctagat taggaaacct cgttcggc                                          28
```